United States Patent
Ye et al.

(10) Patent No.: US 12,282,027 B2
(45) Date of Patent: Apr. 22, 2025

(54) HIGH-THROUGHPUT NMR APPROACH FOR IN-MEMBRANE PROTEIN LIGAND SCREENING

(71) Applicant: University of South Florida, Tampa, FL (US)

(72) Inventors: Libin Ye, Tampa, FL (US); Xudong Wang, Tampa, FL (US)

(73) Assignee: University of South Florida, Tampa, FL (US)

(*) Notice: Subject to any disclaimer, the term of this patent is extended or adjusted under 35 U.S.C. 154(b) by 652 days.

(21) Appl. No.: 17/677,249

(22) Filed: Feb. 22, 2022

(65) Prior Publication Data
US 2022/0283178 A1 Sep. 8, 2022

Related U.S. Application Data

(60) Provisional application No. 63/151,539, filed on Feb. 19, 2021.

(51) Int. Cl.
G01N 33/68 (2006.01)
G01N 1/34 (2006.01)
G01N 24/08 (2006.01)

(52) U.S. Cl.
CPC .......... *G01N 33/6845* (2013.01); *G01N 1/34* (2013.01); *G01N 24/087* (2013.01); *G01N 33/6848* (2013.01)

(58) Field of Classification Search
None
See application file for complete search history.

(56) References Cited

U.S. PATENT DOCUMENTS

| | | | |
|---|---|---|---|
| 7,674,595 | B1 | 3/2010 | Cross et al. |
| 2003/0129649 | A1 | 7/2003 | Kobilka et al. |
| 2007/0134219 | A1 | 6/2007 | Karlsson-Parra et al. |
| 2013/0137856 | A1 | 5/2013 | Steyaert et al. |
| 2013/0216584 | A1 | 8/2013 | Kirkin et al. |
| 2015/0335679 | A1 | 11/2015 | Chiriva-Internati |

OTHER PUBLICATIONS

Yanamala, N. et al. NMR-Based Screening of Membrane Protein Ligands, Chem Biol Drug Des 2010: 75: 237-256 (Year: 2010).*
Andre et al., "Enhancing functional production of G proteincoupled receptors in Pichia pastoris to levels required for structural studies via a single expression screen," Protein Sci, 2006, 15(5):1115-1126.
Auld et al., "Receptor Binding Assays for HTS and Drug Discovery," In: Assay Guidance Manual [Internet], Bethesda (MD): Eli Lilly & Company and the National Center for Advancing Translational Sciences, May 2004-2012, 42 pages.
Broeke et al., "MHC Class II Antigen Presentation by Dendritic Cells Regulated through Endosomal Sorting," Perspect Biol, 2013, 5(12):a016873.

(Continued)

*Primary Examiner* — Xiaoyun R Xu
(74) *Attorney, Agent, or Firm* — Michele L. Lawson; Smith & Hopen, P.A.

(57) ABSTRACT

This disclosure relates to the identification of interactions between ligands and in-membrane proteins using nuclear magnetic resonance spectroscopy. Also provided are methods for high-throughput identification of in-membrane ligand-membrane protein interactions.

12 Claims, 13 Drawing Sheets

(56) References Cited

OTHER PUBLICATIONS

Carpenter et al., "Expression and Purification of Mini G Proteins from *Escherichia coli*," Bio Protocol, Apr. 2017, 7(8):e2235.
Congreve et al., "Impact of GPCR Structures on Drug Discovery," Cell 181(1):81-91.
Dalvit et al., "WaterLOGSY as a method for primary NMR screening: Practical aspects and range of applicability," J Biomol NMR, Dec. 2001, 21:349-359.
Draper-Joyce et al., "Structure of the adenosine-bound human adenosine A1 receptor-Gi complex," Nature, Jun. 2018, 558(7711):559-563.
Dubnau, "DNA uptake in bacteria," Annu Rev Microbiol, 1999, 53:217-244.
Encyclopedia of Biophysics, Roberts G.C.K. eds., Springer, 2013, CPMG, 234 pages.
Gallagher et al., "Immunoblot analysis ," Journal of Visualized Experiments (16), 2008, 1 page.
idtdna.com [online], "IDT Integrated DNA Technologies," available on or before May 2017, retrieved on Mar. 16, 2022, retrieved from URL<https://www.idtdna.com/pages>, 4 pages.
International Preliminary Report on Patentability in International Application No. PCT/US2019/014352, dated Jul. 21, 2020, 12 pages.
International Search Report and Written Opinion in International Application No. PCT/US2019/014352, dated Jun. 10, 2019, 13 pages.
Krettler et al., "Expression of GPCRs in Pichia pastoris for structural studies," Methods Enzymol, 2013, 520: 1-29.
Laemmli, "Cleavage of structural proteins during the assembly of the head of bacteriophage T4," Nature, Aug. 1970, 227(5259):680-685.
Lucio et al., "Drug-membrane interactions: significance for medicinal chemistry," Curr Med Chem, 2010, 17(17):1795-1809.
Mayer et al., "Group Epitope Mapping by Saturation Transfer Difference NMR to Identify Segments of a Ligand in Direct Contact with a Protein Receptor," J Am Chem Soc, Jun. 2001, 123(25):6108-6117.
Nehme et al., "Mini-G proteins: Novel tools for studying GPCRs in their active conformation," PLoS One, Apr. 2017, 12(4):e0175642.
Overington et al., "How many drug targets are there?" Nat Rev Drug Discov, Dec. 2006, 5(12):993-996.
Warschawski et al., "Choosing membrane mimetics for NMR structural studies of transmembrane proteins," Biochimica et Biophysica Acta (BBA)—Biomembranes, Aug. 2011, 1808(8):1957-1974.
Wilson et al., "Dendritic cells constitutively present self antigens in their immature state in vivo and regulate antigen presentation by controlling the rates of MHC class II synthesis and endocytosis," Blood, 2004, 103(6):2187-2195.
Ye et al., "Activation of the A2A adenosine G-protein-coupled receptor by conformational selection," Nature, May 2016, 533(7602):265-268.
Ye et al., "High-Efficiency Expression of Yeast-Derived G-Protein Coupled Receptors and (19)F Labeling for Dynamical Studies," Methods Mol Biol, 1688:407-42.
Ye et al., "Mechanistic insights into allosteric regulation of the A2A adenosine G protein-coupled receptor by physiological cations," Nature Communications, Apr. 2018, 9(1):1372.
Zacca et al., "Aging Impairs the Ability of Conventional Dendritic Cells to Cross-Prime CD8 T cells upon Stimulation with a TLR7 Ligand," PLoS One, Oct. 2015, 20 pages.
Zhao et al., "Expression and Purification of Yeast-derived GPCR, Gα and Gβγ Subunits for Structural and Dynamic Studies," ioprotocol, 2021, 10.
Zhou et al., "Multiple GPCR Functional Assays Based on Resonance Energy Transfer Sensors," Front Cell Dev Biol, May 2021, 10(9):611443.

\* cited by examiner

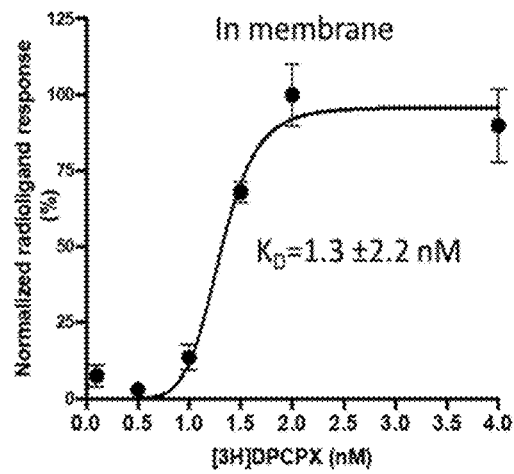
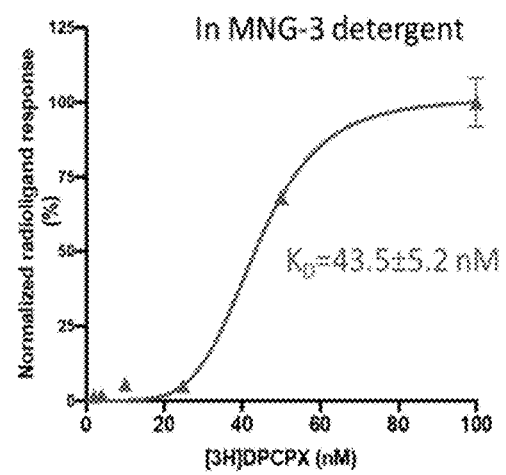
FIG. 1A  FIG. 1B
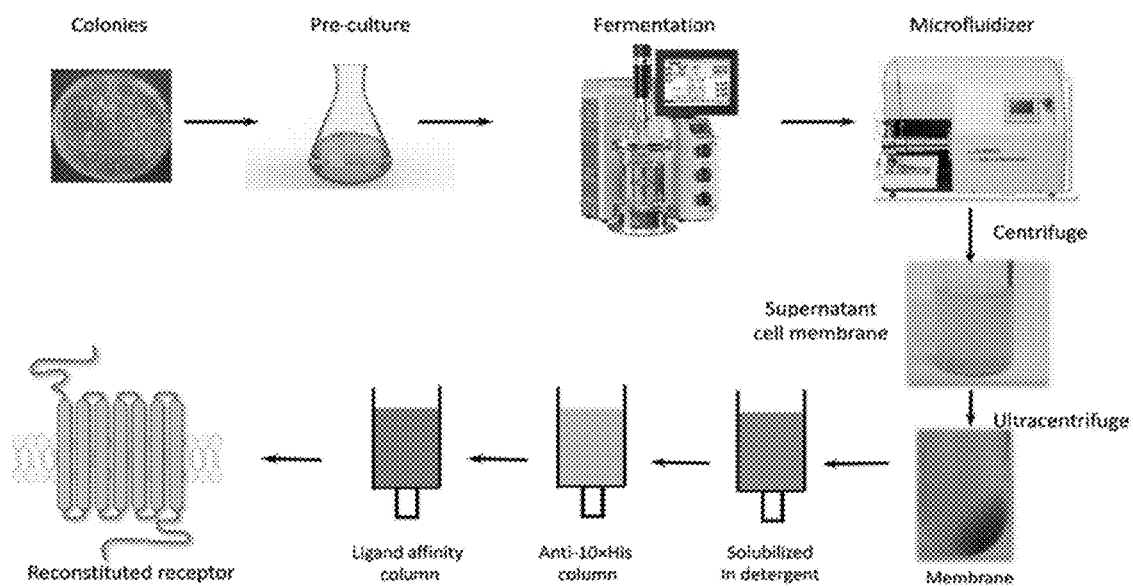
FIG. 2

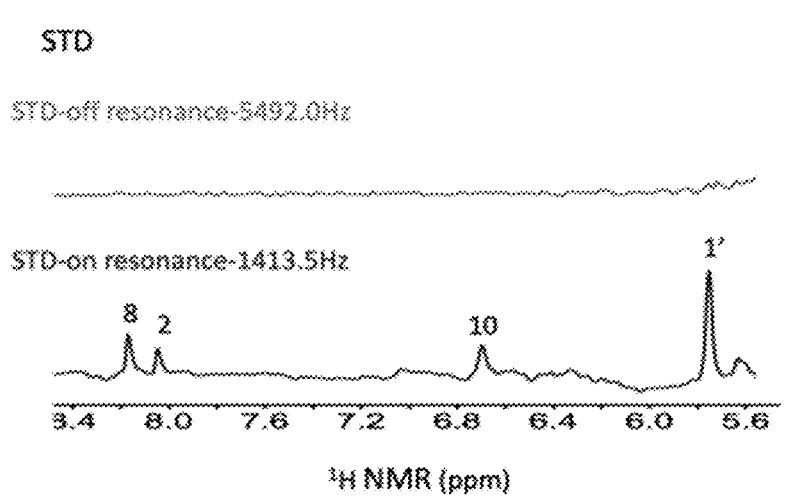
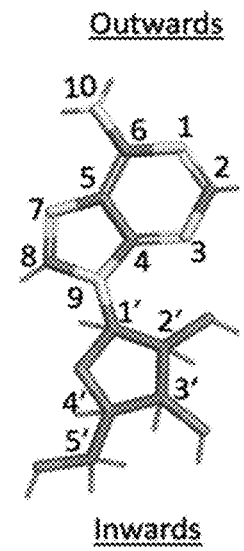
FIG. 4A  FIG. 4B
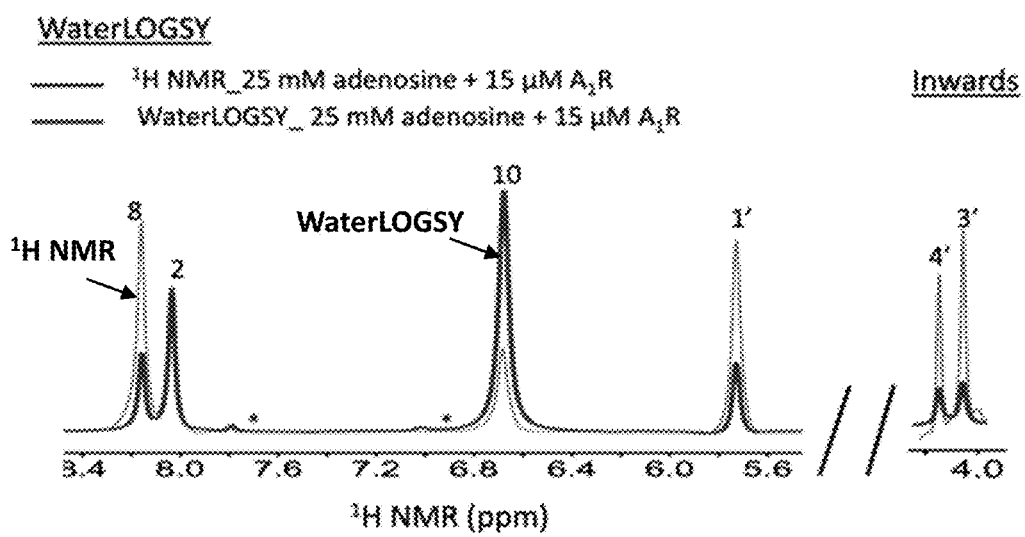
FIG. 4C

HIGH-THROUGHPUT NMR APPROACH FOR IN-MEMBRANE PROTEIN LIGAND SCREENING

CROSS-REFERENCE TO RELATED APPLICATION

This application claims priority to U.S. Provisional Application No. 63/151,539, filed Feb. 19, 2021, which is incorporated herein by reference in its entirety.

TECHNICAL FIELD

This disclosure relates to the identification of ligand-membrane protein interactions using nuclear magnetic resonance spectroscopy, and more particularly to high-throughput identification of ligand-membrane protein interactions.

BACKGROUND

Conventional approaches for studying ligand-membrane protein interactions are often tedious and time consuming and can involve elaborative membrane protein preparations to obtain a sufficient amount for studying via NMR. Isotopic labeling and reconstitution are often prerequisites to measure ligand-membrane protein interaction using NMR, but such systems are still a "black box" as to whether they faithfully reflect the natural ligand-membrane protein interaction in the membrane. On the other hand, in-cell NMR is still being developed and is impeded by instrumental limitations for large scale applications.

Conventional cell-based high throughput drug screening is increasingly driven by the integration of a virtual computation-assisted and structure-based screening components using online open platforms like ZINC, SwissDock, and Enamine REAL. In pursuing these predicted "hits", the faithfulness of probed ligand-receptor interaction in the validation step is key to identifying desirable candidates. Accurately determining the functionality of a ligand remains challenging due to the intrinsic limitations of either resolved or simulated structures. One barrier includes the conformational heterogeneity and functional diversity that are reduced during homogeneity processing and thermo-stabilization in structural determination. These structures can impair computation-based molecular dynamics (MD) and virtual drug screening when used as starting models. Additionally, these structures can be incomplete due to flexible domains and missed amino acid sidechain information. Determining all candidate ligand structures and functionality in complex with membrane proteins has been unrealistic and infeasible due to the scale. Recent progress toward de novo construction of complete GPCR structures using modeling and simulation has been achieved, but further validation is required regarding the accuracy and representability of these simulated structures. Therefore, approaches that can retain receptor heterogeneity and functional diversity are in great demand.

Additionally, obtaining a large quantity of purified receptors and ligands has conventionally been a prerequisite to ascertaining ligand-membrane protein interactions using NMR. Extracting membrane proteins from native bilayer lipids and reconstituting them into a lipid bilayer mimic system can raise fidelity concerns; removing membrane proteins from their native environments can result in unknown functional changes. Meanwhile, $^{13}C/^{15}N$ isotopic labeling, which is often used for studying ligand-membrane protein interactions, poses additional challenges for eukaryotic expression systems for preparing high quantities of membrane proteins for NMR, as it can be time-consuming and costly. New assay methods are desirable.

SUMMARY

Provided herein is a method of identifying a ligand able to bind to an in-membrane protein, the method including: contacting an in-membrane protein with a ligand; and detecting one or more NMR signals of the ligand; wherein a decrease in one or more NMR signals of the ligand in the presence of the in-membrane protein relative to the NMR signals of the ligand in the absence of the in-membrane protein indicates that the ligand binds to the in-membrane protein.

Also provided herein is a method of detecting binding of a ligand to an in-membrane protein, the method including: contacting an in-membrane protein with a ligand; and detecting one or more NMR signals of the ligand; wherein a decrease in one or more NMR signals of the ligand in the presence of the in-membrane protein relative to the NMR signals of the ligand in the absence of the in-membrane protein indicates that the ligand binds to the in-membrane protein.

Also provided herein is a method of identifying a ligand able to bind to an in-membrane protein, the method comprising: contacting an in-membrane protein with a ligand; detecting one or more NMR signals of the ligand using Water-Ligand Observed via Gradient SpectroscopY (WaterLOGSY); and detecting one or more NMR signals of the ligand using regular $^1H$ NMR, wherein a decrease in one or more NMR signals of the ligand obtained using WaterLOGSY relative to the NMR signals of the ligand obtained using regular $^1H$ NMR indicates that the ligand binds to the in-membrane protein.

Also provided herein is a method of detecting binding of a ligand to an in-membrane protein, the method comprising: contacting an in-membrane protein with a ligand; detecting one or more NMR signals of the ligand using WaterLOGSY; and detecting one or more NMR signals of the ligand using regular $^1H$ NMR, wherein a decrease in one or more NMR signals of the ligand obtained using WaterLOGSY relative to the NMR signals of the ligand obtained using regular $^1H$ NMR indicates that the ligand binds to the in-membrane protein.

Also provided herein is a method of detecting binding of a ligand to an in-membrane protein, the method comprising: contacting an in-membrane protein with a ligand; detecting one or more NMR signals of the ligand using WaterLOGSY; and determining one or more effective negative NOE signals, wherein a decrease in one or more NMR signals of the ligand obtained using WaterLOGSY relative to the NMR signals of the ligand obtained using regular $^1H$ NMR indicates that the ligand binds to the in-membrane protein. In some embodiments, determining one or more effective negative NOE signals comprises subtracting a reference spectrum from the WaterLOGSY spectrum of the ligand (e.g., the ligand in the presence of the in-membrane protein). In some embodiments, the reference spectrum is a $^1H$ NMR spectrum of the ligand (e.g., the ligand in the presence of the in-membrane protein). In some embodiments, the reference spectrum is a WaterLOGSY spectrum of the ligand in the presence of a membrane fragment.

In some embodiments, the method includes the use of high-throughput screening. In some embodiments, the ligand is from a library of ligands. In some embodiments, the method is a high-throughput screening method further including distributing a plurality of ligands into a plurality of individual vessels, wherein each vessel can include an in-membrane protein.

Also provided herein is a method of screening ligands for binding to an in-membrane protein, the method including contacting an in-membrane protein with a plurality of ligands; and detecting one or more NMR signals of the ligands; wherein a decrease in one or more NMR signals of a ligand in the presence of an in-membrane protein indicates that the ligand binds to the in-membrane protein.

In some embodiments, the in-membrane protein is selected from the group consisting of: an adhesion protein (e.g., an integrin, cadherin, or NCAM), a selectin, a receptor, or an ion channel. In some embodiments, the in-membrane protein is an in-membrane GPCR. In some embodiments, the in-membrane GPCR is selected from the group consisting of: a Class A-rhodopsin-like receptor, a Class B-secretin family receptor, a Class C-metabotropic glutamate receptor, a Class D-fungal mating pheromone receptor, a class E-cAMP receptor, and a Class F-frizzled and smoothened receptor. In some embodiments, the GPCR is selected from the group consisting of: a serotonin olfactory receptor, a glycoprotein hormone receptor, chemokine receptor, an adenosine receptor, a biogenic amine receptor, a melanocortin receptor, a neuropeptide receptor, a chemotactic receptor, a somatostatin receptor, an opioid receptor, a melatonin receptor, a calcitonin receptor, a PTH/PTHrP receptor, a glucagon receptor, a secretin receptor, a latrotoxin receptor, a metabotropic glutamate receptor, a calcium receptor, a GABA-B receptor, a pheromone receptor, a protease-activated receptor, and a rhodopsin.

In some embodiments, the in-membrane GPCR is prepared by disrupting cell membranes of a cell culture that expresses the GPCR and removing the debris. Disrupting the cell membranes can include using one or more of: a microfluidizer, glass beads, a sonicator, a French press, and enzymatic methods. In some embodiments, breaking buffer is added to the cell culture prior to disrupting the cell membranes. In some embodiments, the debris is removed by centrifugation.

In some embodiments, detecting the one or more NMR signals of the ligand can include obtaining an NMR spectrum of the ligand in the presence of an in-membrane protein. In some embodiments, the one or more NMR signals of the ligand can be determined using WaterLOGSY, Carr-Purcell-Meiboom-Gill (CPMG), saturation transfer difference (STD). In some embodiments, the NMR signals of the ligand in the absence of the in-membrane protein can be determined using a reference NMR spectrum of the ligand in the absence of the in-membrane protein.

In some embodiments, the method can further include obtaining an NMR spectrum of the ligand in the absence of an in-membrane protein. Obtaining the NMR spectrum of the ligand can include using WaterLOGSY. In some embodiments, the methods described herein can further include determining the solvent exposure of the ligand bound to the in-membrane protein. In some embodiments, the methods described herein further include determining the orientation of the ligand bound to the in-membrane protein. In some embodiments, the ligand has a dissociation rate of about 1 nM to about 10 mM.

In some embodiments, the decrease in the one or more NMR signals of the ligand can be by about 5% to about 100%.

In some embodiments, the method further includes determining a change in the chemical shift of one or more NMR signals of the ligand in the presence of the in-membrane protein relative to chemical shift of the one or more NMR signals of the ligand in the absence of the in-membrane protein. In some embodiments, the method can further include using the one or more NMR signals of the ligand bound to the in-membrane protein to evaluate a molecular dynamics (MD) simulation of the in-membrane protein and ligand. In some embodiments, the method can further include using the one or more NMR signals of the ligand bound to the in-membrane protein in an MD simulation to refine a structure of the in-membrane protein bound to the ligand.

In some embodiments, disclosed herein is a method of identifying a ligand able to bind to an in-membrane protein, the method including preparing an in-membrane protein; contacting the in-membrane protein with a ligand; detecting one or more NMR signals of the ligand; and determining one or more of: binding orientation, kinetics, and dynamics of the ligand; wherein a decrease in one or more NMR signals of the ligand in the presence of the in-membrane protein relative to the NMR signals of the ligand in the absence of the in-membrane protein indicates that the ligand binds to the in-membrane protein.

In some embodiments, disclosed herein is a method of detecting binding of a ligand to an in-membrane protein, the method including: preparing an in-membrane protein; contacting the in-membrane protein with a ligand; detecting one or more NMR signals of the ligand; and determining one or more of: binding orientation, kinetics, and dynamics of the ligand; wherein a decrease in one or more NMR signals of the ligand in the presence of the in-membrane protein relative to the NMR signals of the ligand in the absence of the in-membrane protein indicates that the ligand binds to the in-membrane protein.

In some embodiments, disclosed herein is a method of screening ligands for binding to an in-membrane protein, the method including: preparing an in-membrane protein;

contacting the in-membrane protein with a ligand; detecting one or more NMR signals of the ligand; and determining one or more of: binding orientation, kinetics, and dynamics of the ligand; wherein a decrease in one or more NMR signals of the ligand in the presence of the in-membrane protein relative to the NMR signals of the ligand in the absence of the in-membrane protein indicates that the ligand binds to the in-membrane protein.

The details of one or more embodiments of the invention are set forth in the accompanying drawings and the description below. Other features, objects, and advantages of the invention will be apparent from the description and drawings, and from the claims.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIGS. 1A and 1B are radioligand binding assay curves for the receptors in native membrane and MNG-3 detergent systems.

FIG. 2 is a schematic diagram of a conventional receptor preparation procedure reconstituted in a reconstitution system such as detergent MNG-3 and high density lipoprotein (HDL) systems.

FIG. 4A is a saturation transfer difference spectrum of adenosine interacting with the $A_1R$ receptor. FIG. 4B is an observed proton numbering of adenosine in the spectrum of FIGS. FIG. 4C has a WaterLOGSY spectrum of adenosine-$A_1R$ interaction (denoted by the darker line) in reference to $^1$H NMR. The negative WaterLOGSY signals were flipped into the positive for comparison purpose.

DETAILED DESCRIPTION

Figure 3A:
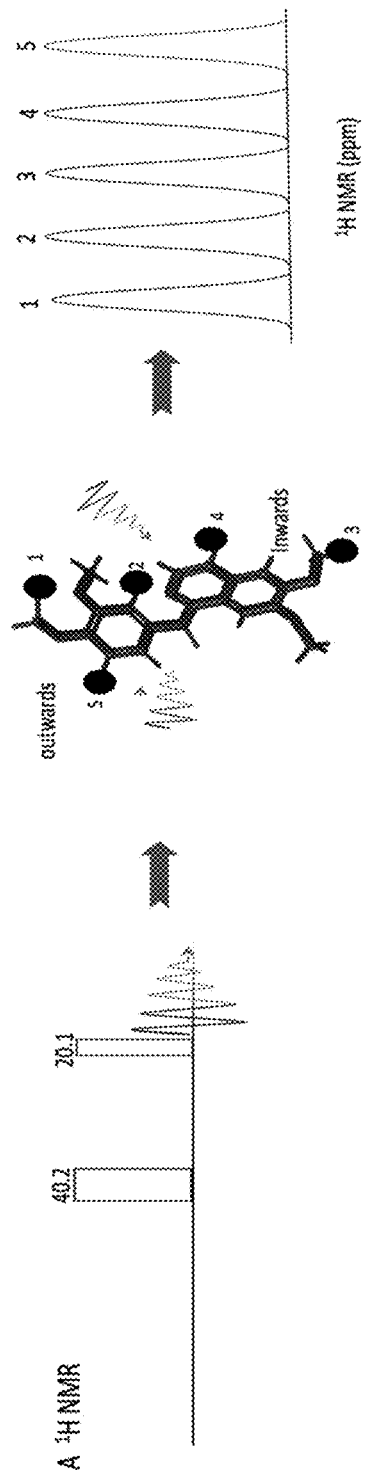
FIG. 3A is a schematic flowchart of $^1$H NMR used as a reference for WaterLOGSY NMR in probing ligand orientation binding to receptor pocket.

Disclosed herein are methods of identifying ligands able to bind to in-membrane proteins. As used herein, "able to bind" refers to a molecule that is capable of forming a direct binding interaction with a protein, i.e., that is detectable using the NMR techniques described herein. Also provided herein are methods for detecting binding of a ligand to an in-membrane protein. In some embodiments, provided herein are methods for detecting molecular interactions, binding orientation, kinetics, and dynamics of the ligand bound to an in-membrane protein. Such methods can include using NMR spectroscopy to determine one or more of binding, binding orientation, molecular interactions, kinetics, and dynamics of the ligand bound to the in-membrane protein. For example, the methods described herein can include contacting an in-membrane protein with a ligand; and detecting one or more NMR signals of the ligand, wherein a decrease in one or more NMR signals of the ligand in the presence of the in-membrane protein relative to the NMR signals of the ligand in the absence of the in-membrane protein indicates that the ligand binds to the in-membrane protein. In some embodiments, the methods described herein include contacting an in-membrane protein with a ligand; detecting one or more NMR signals of the ligand using WaterLOGSY; and detecting one or more NMR signals of the ligand using regular $^1$H NMR, wherein a decrease in one or more NMR signals of the ligand obtained using WaterLOGSY relative to the NMR signals of the ligand obtained using regular $^1$H NMR indicates that the ligand binds to the in-membrane protein.

Also provided herein are methods of detecting binding of a ligand to an in-membrane protein, the method comprising: contacting an in-membrane protein with a ligand; detecting one or more NMR signals of the ligand using WaterLOGSY; and determining one or more effective negative NOE signals, wherein a decrease in one or more NMR signals of the ligand obtained using WaterLOGSY relative to the NMR signals of the ligand obtained using regular $^1$H NMR indicates that the ligand binds to the in-membrane protein.

As used herein, an "in-membrane protein" refers to a recombinant transmembrane protein in a native membrane. For example, an in-membrane protein as described herein can be a recombinant transmembrane protein fractionated from a cell culture with a membrane fragment, e.g., the membrane protein is still embedded in the fragment of the native bilayer lipid system from the cell. These methods can be useful, for example, for maintaining membrane protein structural heterogeneity and/or facilitating high-throughput drug screening as well as simplifying sample preparation of membrane proteins. Additionally, these methods can allow for the use of solution-state NMR spectroscopy to study the interaction of a ligand and an in-membrane protein rather than solid-state NMR spectroscopy, which is typically needed to study a transmembrane protein in an intact cell.

In some embodiments of the methods described herein, the method comprises the use of high-throughput screening. For example, a plurality of ligands can be screened for binding against in-membrane proteins. In some embodiments, a plurality of ligands are distributed into a plurality of individual vessels, wherein each vessel comprises an in-membrane protein. In some embodiments, each individual vessel comprises the same in-membrane protein. In some embodiments, one or more individual vessels comprise a different in-membrane protein than one or more other individual vessels. In some embodiments, the ligand is from a library of ligands. In some embodiments, the library is a commercially-available library. Accordingly, also provided herein are methods of screening ligands for binding to an in-membrane protein, the method comprising: contacting an in-membrane protein with a plurality of ligands; and detecting one or more NMR signals of the ligands; wherein a decrease in one or more NMR signals of the ligand in the presence of the in-membrane protein relative to the NMR signals of the ligand in the absence of the in-membrane protein (i.e., a decrease in the signal intensity of one or more NMR signals of the ligand) indicates that the ligand binds to the in-membrane protein. In some embodiments, provided herein are methods of screening ligands for binding to an in-membrane protein, the method comprising: contacting an in-membrane protein with a plurality of ligands; detecting one or more NMR signals of the ligands using Water-LOGSY; and detecting one or more NMR signals of the ligands using regular $^1$H NMR, wherein a decrease in one or more NMR signals of the ligands obtained using water LOGSY relative to the NMR signals of the ligands obtained using regular $^1$H NMR indicates that the ligand binds to the in-membrane protein.

In some embodiments, about 1 to about 5000 ligands are screened in one day. For example, about 1 to about 100, about 1 to about 500, about 1 to about 1000, about 1 to about 2500, about 2500 to about 5000, about 1000 to about 5000, about 500 to about 5000, or about 100 to about 5000 ligands are screened in one day. In some embodiments, 100 or more, 500 or more, 750 or more, or 1000 or more ligands are screened in one day.

An in-membrane protein as described herein can be expressed by routine recombinant methods, e.g., culturing cells transformed or transfected with a nucleic acid construct (e.g., an expression vector) containing a nucleotide sequence encoding the transmembrane protein. Numerous expression systems can be used to produce an in-membrane protein as described herein. Non-limiting examples of expression systems include insect cell/baculovirus systems and mammalian expression systems. In some embodiments, the expression system is a yeast cell line. In some embodiments, the yeast cell line is *Pichia pastoris*. In some embodiments, the expression system is a mammalian cell line such as HEK293. In some embodiments, the expression system is an insect cell line such as sf9.

Any transmembrane protein can be used in the methods described herein. Non-limiting examples of transmembrane proteins include: adhesion proteins (e.g., integrins, cadherins, NCAMs), selectins, receptors, transporters, and ion channels. Non-limiting examples of receptors include ion channel-linked receptors, G-protein-linked receptors (GPCRs), or enzyme-linked receptors. In some embodiments, the in-membrane protein is an in-membrane GPCR. GPCRs are typically classified into 6 categories: Class A-rhodopsin-like receptors, Class B-secretin family receptors, Class C-metabotropic glutamate receptors, Class D-fungal mating pheromone receptors, class E-cAMP receptors, and Class F-frizzled and smoothened receptors. In some embodiments, the GPCR is selected from the group consisting of: a serotonin olfactory receptor, a glycoprotein hormone receptor, chemokine receptor, an adenosine receptor, a biogenic amine receptor, a melanocortin receptor, a neuropeptide receptor, a chemotactic receptor, a somatostatin receptor, an opioid receptor, a melatonin receptor, a calcitonin receptor, a PTH/PTHrP receptor, a glucagon receptor, a secretin receptor, a latrotoxin receptor, a metabotropic glutamate receptor, a calcium receptor, a GABA-B receptor, a pheromone receptor, a protease-activated receptor, and a rhodopsin.

In some embodiments of the methods described herein, the method further includes preparing the in-membrane protein. For example, in some embodiments, the methods described herein include disrupting cell membranes of a cell culture that expresses a transmembrane protein and removing the debris. The disrupted cell membranes (e.g., membrane fragments) can include the expressed transmembrane protein. In some embodiments, such transmembrane proteins are the in-membrane proteins described herein. Any method for disrupting cell membranes can be used. For example, disrupting the cell membrane can comprise using one or more of a microfluidizer, glass beads, steel beads, ceramic beads, cryopulverization, high pressure (e.g., a French press, pressure cycling technology, or microfluidizer), sonication, and nitrogen decompression. In some embodiments, disrupting the cell membrane comprises using a microfluidizer or glass beads. In some embodiments, disrupting the cell membrane comprises using an enzymatic method. In some embodiments, the enzymatic method uses lysozyme to disrupt the cell walls.

In some embodiments, a breaking buffer is added to the cell culture prior to disrupting the cell membranes. In some embodiments, the breaking buffer comprises; 50 mM HEPES, pH 7.4, 100 mM NaCl, 2 mM EDTA, 10% glycerol.

In some embodiments, the debris (e.g., unbroken cells) is removed by centrifugation. For example, after disrupting the cell membranes, the disrupted cells can be centrifuged at about 9,720×g. In some embodiments, the disrupted cells are centrifuged for about 30 minutes. The supernatant after centrifugation can contain a disrupted cell membrane (e.g., a membrane fragment) comprising an expressed transmembrane protein, e.g., an in-membrane protein as described herein.

In some embodiments of the methods described herein, the method further includes diluting a disrupted cell membrane (e.g., a membrane fragment) comprising an expressed transmembrane protein, e.g., an in-membrane protein as described herein. For example, after disrupted cells are centrifuged, the supernatant containing disrupted cell membranes comprising an expressed transmembrane protein, e.g., an in-membrane protein as described herein, can be diluted. In some embodiments, the in-membrane protein is diluted about 1 fold to about 20 fold. For example, about 1 fold to about 5 fold, 1 fold to about 10 fold, 1 fold to about 15 fold, 5 fold to about 10 fold, 5 fold to about 15 fold, 5 fold to about 20 fold, 10 fold to about 15 fold, 10 fold to about 20 fold, or about 15 fold to about 20 fold. In some embodiments, the in-membrane protein is diluted about 1 fold, about 2 fold, about 3 fold, about 4 fold, about 5 fold, about 6 fold, about 7 fold, about 8 fold, about 9 fold, about 10 fold, about 11 fold, about 12 fold, about 13 fold, about 14 fold, about 15 fold, about 16 fold, about 17 fold, about 18 fold, about 19 fold, or about 20 fold. In some embodiments, the in-membrane protein is diluted prior obtaining an NMR spectrum of a ligand in the presence of the in-membrane protein. Diluting the in-membrane protein can be useful to, for example, reduce NOE transfer not involving the in-membrane protein. For example, dilution can reduce NOE transfer involving transmembrane proteins that are native to the cell membrane and/or not expressed through recombinant methods in the cell membrane.

In some embodiments, the methods described herein can further include the preparation of a membrane fragment that does not comprise an in-membrane protein as described herein (e.g., an in-membrane protein expressed using recombinant methods). For example, a membrane fragment can be prepared using the methods described above from a cell culture that does not express a recombinant transmembrane protein.

NMR spectroscopy can be used in the methods described herein to probe interactions between a ligand and in-membrane protein. Any NMR pulse sequence that can be used to detect interactions between ligands and in-membrane proteins can be used in the methods described herein. Non-limiting examples of such NMR pulse sequences include saturation transfer difference (STD), Carr-Purcell-Meiboom-Gill (CPMG), WaterLOGSY, and regular $^1$H NMR (see, FIG. 3A). For example, WaterLOGSY uses bulky water nuclear Overhauser effect (NOE) mediation from the in-membrane protein to the ligand and a decrease in one or more NMR signals of the ligand in the presence of an in-membrane protein relative to the NMR signals of the ligand in the absence of the in-membrane protein or NMR signals from one or more other reference spectra can indicate binding the ligand to the in-membrane protein. For descriptions of pulse sequences described herein, see, e.g., Dalvit C, et al., WaterLOGSY as a method for primary NMR screening: practical aspects and range of applicability. J Biomol NMR. 2001; 21:349-359; Mayer M, Meyer B., Group Epitope Mapping by Saturation Transfer Difference NMR. To Identify Segments of a Ligand in Direct Contact with a Protein Receptor. J Am Chem Soc. 2001; and P. McIntosh L. (2013) CPMG. In: Roberts G.C.K. (eds) Encyclopedia of Biophysics. Springer, Berlin, Heidelberg., doi.org/10.1007/978-3-642-16712-6_320, the contents of which are hereby incorporated by reference in their entirety.

In some embodiments of the methods described herein, an NMR spectrum is acquired using a 600 MHz NMR spectrometer. For example, a $^1$H and/or $^{19}$F NMR spectra can be acquired on a 600 MHz NMR spectrometer such as a 600 MHz Varian Inova spectrometer. In some embodiments, a cryogenic triple resonance probe is used to acquire an NMR spectrum described herein. In some embodiments, the high-frequency channel is tuned to $^1$H. In some embodiments, the high-frequency channel is tuned to $^{19}$F. In some embodiments, the H$_2$O signal in $^1$H can be suppressed using the saturation pulse incorporated into a t2pul sequence. In some embodiments, detecting one or more NMR signals of the ligand can include obtaining an NMR spectrum of the ligand using any of the pulse sequences described herein. In some embodiments, obtaining an NMR spectrum of the ligand can include obtaining an NMR spectrum of the ligand in the absence of an in-membrane protein. In some embodiments, obtaining an NMR spectrum of the ligand can include obtaining an NMR spectrum of the ligand in the presence of an in-membrane protein.

In some embodiments of the methods described herein, one or more NMR signals of the ligand in the presence of an in-membrane protein can be compared to the NMR signals of the ligand in the absence of the in-membrane protein. In some embodiments, the same pulse sequence is used to obtain the NMR signals of the ligand in the presence and the absence of the in-membrane protein. In some embodiments, a different pulse sequence is used to obtain the NMR signals of the ligand in the presence compared to the absence of the in-membrane protein. For example, in some embodiments, a WaterLOGSY pulse sequence can be used to obtain one or more NMR signals of the ligand in the presence of the in-membrane protein and regular $^1$H NMR can be used to obtain the NMR signals of the ligand in the absence of the in-membrane protein.

In some embodiments of the methods described herein, one or more NMR signals from a first spectrum of the ligand in the presence of an in-membrane protein can be compared to the NMR signals from a second spectrum of the ligand in the presence of the in-membrane protein. In some embodiments, a different pulse sequence is used to obtain the first spectrum than the pulse sequence used to obtain the second spectrum. For example, in some embodiments, regular $^1$H NMR can be used to obtain the first spectra (e.g., one or more NMR signals) of the ligand in the presence of the in-membrane protein and Water LOGSY can be used to obtain the second spectra (e.g., NMR signals) of the ligand in the presence of the in-membrane protein.

In some embodiments of the methods described herein, one or more NMR signals of the ligand in the presence of an in-membrane protein can be compared to the NMR signals of one or more reference spectra. A reference NMR spectrum can include, for example, an NMR spectrum of the ligand in the absence of the in-membrane protein or an NMR spectrum of the ligand in the absence of the in-membrane protein but in the presence of a membrane fragment (e.g., any of the membrane fragments as described herein). In some embodiments, wherein the one or more NMR signals of the ligand in the presence of the in-membrane protein is determined using WaterLOGSY (e.g., a WaterLOGSY spectrum of the ligand in the presence of the in-membrane protein is acquired), the regular $^1$H spectrum of the ligand in the presence of the in-membrane protein can be a reference spectrum. In some embodiments, a reference NMR spectrum includes an NMR spectrum of the in-membrane protein in the absence of the ligand, an NMR spectrum of one or more solvents in the absence of the in-membrane protein and the absence of the ligand.

In some embodiments, one or more NMR signals from a WaterLOGSY spectrum of the ligand in the presence of the in-membrane protein is compared to one or more signals of a WaterLOGSY spectrum of the ligand in the presence of a membrane fragment, e.g., a membrane fragment that does not comprise the in-membrane protein. In some embodiments, one or more signals of a WaterLOGSY spectrum of the ligand in the presence of a membrane fragment, e.g., a membrane fragment that does not comprise the in-membrane protein, is subtracted from one or more NMR signals from a WaterLOGSY spectrum of the ligand in the presence of the in-membrane protein. Subtracting a WaterLOGSY spectrum of the ligand in the presence of a membrane fragment, e.g., a membrane fragment that does not comprise the in-membrane protein, from a WaterLOGSY spectrum of the ligand in the presence of the in-membrane protein can be useful for, for example, removing NOE transfer not involving the in-membrane protein.

In some embodiments, a decrease in one or more NMR signals of the ligand in the presence of the in-membrane protein, relative to the NMR signals of the ligand in the absence of the in-membrane protein (i.e., a decrease in the signal intensity of one or more NMR signals of the ligand) indicates that the ligand binds to the in-membrane protein. In some embodiments, a decrease in one or more NMR signals of the ligand in the presence of the in-membrane protein, wherein the NMR spectrum is obtained using WaterLOGSY, relative to the NMR signals of the ligand in the absence of the in-membrane protein, wherein the NMR spectrum is obtained using WaterLOGSY or regular $^1$H NMR, indicates that the ligand binds to the in-membrane protein.

In some embodiments, the decrease in one or more NMR signals of the ligand in the presence of the in-membrane protein relative to the NMR signals of the ligand in the absence of the in-membrane protein or relative to another reference spectra as described herein is by about 5% to about 100%. For example, by about 5% to about 90%, 5% to about 80%, about 5% to about 70%, 5% to about 60%, about 5% to about 50%, about 5% to about 40%, about 5% to about 30%, about 5% to about 20%, about 5% to about 10%, about 10% to about 100%, about 20% to about 100%, about 30% to about 100%, about 40% to about 100%, about 50% to about 100%, about 60% to about 100%, about 70% to about 100%, about 80% to about 100%, about 90% to about 100%, about 10% to about 90%, about 20% to about 80%, about 30% to about 70%, about 40% to about 60%, or about 40% to about 50%).

In some embodiments, a decrease in one or more NMR signals from a first spectrum of the ligand in the presence of the in-membrane protein, relative to the NMR signals from a second spectrum of the ligand in the presence of the in-membrane protein (i.e., a decrease in the signal intensity of one or more NMR signals of the ligand) indicates that the ligand binds to the in-membrane protein. In some embodiments, the decrease in one or more NMR signals from a first spectrum of the ligand in the presence of the in-membrane protein relative to the NMR signals from a second spectrum of the ligand in the presence of the in-membrane protein is by about 5% to about 100%. For example, by about 5% to about 90%, 5% to about 80%, about 5% to about 70%, 5% to about 60%, about 5% to about 50%, about 5% to about 40%, about 5% to about 30%, about 5% to about 20%, about 5% to about 10%, about 10% to about 100%, about 20% to about 100%, about 30% to about 100%, about 40% to about 100%, about 50% to about 100%, about 60% to about 100%, about 70% to about 100%, about 80% to about 100%, about 90% to about 100%, about 10% to about 90%, about 20% to about 80%, about 30% to about 70%, about 40% to about 60%, or about 40% to about 50%). In some embodiments, the first NMR spectrum is obtained using WaterLOGSY and the second NMR spectrum is obtained using regular $^1$H NMR.

Probing interactions between a ligand and in-membrane protein can include determining the solvent exposure of the ligand bound to the in-membrane protein. For example, in some embodiments, a decrease in one or more NMR signals of the ligand in the presence of the in-membrane protein relative to the NMR signals of the ligand in the absence of the in-membrane protein or relative to another reference spectra can be used to determine the solvent exposure of one or more protons of the ligand. In some embodiments, a greater decrease in an NMR signal of the ligand (e.g., a decrease in the NMR signal of the ligand in the presence of the in-membrane protein relative to the NMR signal of the ligand in the absence of the in-membrane protein) relative to the decrease in other NMR signals of the ligand is indicative of less solvent exposure for corresponding proton of the ligand.

Probing interactions between a ligand and in-membrane protein can also include determining the orientation of the ligand bound to the in-membrane protein. In some embodiments, the methods described herein can be used to determine the orientation of the ligand with respect to the in-membrane protein. For example, the orientation of the ligand with respect to the in-membrane protein can include the rotational orientation, or the translational orientation, of the ligand along one or more axes with respect to the in-membrane protein. In some embodiments, a proton of the ligand that is less solvent exposed compared to another proton of the ligand is oriented into the in-membrane protein and away from the solvent.

In some embodiments, the dissociation rate of the ligand is about 1 nM to about 10 mM. For example, about 10 nM to about 10 mM, about 100 nM to about 10 mM, about 1 µM to about 10 mM, about 10 µM to about 10 mM, about 100 µM to about 10 mM, about 1 mM to about 10 mM, about 1 nM to about 1 mM, about 1 nM to about 100 µM, about 1 nM to about 10 µM, about 1 nM to about 1 µM, about 1 nM to about 100 nM, about 1 nM to about 10 nM, about 10 nM to about 1 mM, about 100 nM to about 100 µM, or about 1 µM to about 10 µM). In some embodiments, the methods described herein can be used to determine one or more binding parameters such as dissociation rates of the ligand and in-membrane protein.

In some embodiments, the one or more NMR signals of the ligand bound to the in-membrane protein can be used to evaluate a molecular dynamics (MD) simulation of the in-membrane protein and ligand. An MD simulation as described herein can be performed using a microcanonical ensemble (NVE), canonical ensemble (NVT), isothermal-isobaric (NPT) ensemble, or other generalized ensembles. For example, an MD simulation can be performed using Abalone, ADF, Ascalaph Designer, Avogadro, BOSS, CHARMM, CHEMKIN, CP2K, Desmond, Discovery Studio, fold.it, FoldX, GROMACS, GROMOS, LAMMPS, MacroModel, MAPS, Materials Studio, MBN Explorer, MBN Studio, MDynaMix, MOE, Orac, NAMD, VMD, NWChem, Protein Local Optimization Program, Q, SAMSON, Scigress, Spartan, TeraChem, TINKER, Tremolo-X, Chimera, or YASARA MD simulation systems.

In some embodiments, the one or more NMR signals of the ligand bound to the in-membrane protein is used in an MD simulation to refine a structure of the in-membrane protein bound to the ligand. For example, an MD simulation of a ligand-protein interaction can provide more than one simulated outcomes including stoichiometries, relative orientations, relative rotations, or relative positions between the ligand and protein. The one or more NMR signals can be used, for example, to select, or exclude, one or more of the simulated outcomes.

In some embodiments of any of the methods described herein, the method further comprises performing an in vitro binding assay. Non-limiting examples of such assays include scintillation proximity (SPA) (e.g., a radioligand assay), filtration binding and fluorescence polarization (FP). See, e.g., Receptor Binding Assays for HTS and Drug Discovery. Auld et al. In: Assay Guidance Manual [Internet]. Bethesda (MD): Eli Lilly & Company and the National Center for Advancing Translational Sciences; 2004-2012, which is incorporated by reference herein in its entirety. Such assay can be used, for example, to further validate binding of a ligand to an in-membrane protein.

In some embodiments of any of the methods described herein, the method further comprises performing a functional assay. Such assays can be useful for, for example, determining whether a ligand that binds to an in-membrane protein can also modulate (e.g., inhibit or activate) the activity of the in-membrane protein. Determining whether a ligand modulates the activity of an in-membrane protein can be, for example, helpful for determining whether a ligand could be used in the treatment of a disease. Non-limiting examples of functional assays include those described in Multiple GPCR Functional Assays Based on Resonance Energy Transfer Sensors, Zhou et al. Front Cell Dev Biol. 2021 May 10; 9:611443, which is incorporated by reference herein in its entirety.

EXAMPLES

Example 1

High-Throughput NMR Identification of Ligand-GPCR Interactions

A high-throughput solution-state nuclear magnetic resonance (NMR) method was developed that identifies ligand binding states in in-membrane proteins such as G protein-coupled receptors (GPCR). The results of this method were compared to molecular dynamics ligand-binding solutions to validate the orientation and hydration of the ligand.

Materials and Methods

Protein Expression and Receptor Membrane Preparation

The human $A_1$ receptor and $A_{2A}$ receptor were cloned into pPIC9K with an N-terminal Flag tag and a C-terminal His tag. The proteins were expressed using *Pichia pastoris* (ATCC®28485™; Invitrogen, CA, USA). After 60 h methanol induction in BMMY medium [1% (w/v) yeast extract, 2% (w/v) peptone, 1.34% (w/v) YNB without amino acids, 0.00004% (w/v) biotin, 0.5% (w/v) methanol, 0.1 M phosphate buffer at pH 6.5, 0.04% (w/v) histidine and 3% (v/v) DMSO, 10 mM theophylline] at 20° C., cells were disrupted by Microfluidizer LM20 in breaking buffer (50 mM HEPES, pH 7.4, 100 mM NaCl, 2 mM EDTA, 10% glycerol, 100 µM theophylline). The lysed cell pellets were centrifuged at 9,720×g for 30 min to remove all debris and keep the released membrane fraction parts. The expression and purification of mini-Gi and mini-Gs protein were performed based on a published method (see Nehmé R, et al. PLoS One. 2017; 12(4):e0175642. doi: 10.1371/journal.pone.0175642. eCollection 2017; Carpenter B, and Tate C G. Bio Protoc. 2017; 7(8):e2235. doi: 10.21769/BioProtoc.2235).

Receptor Purification

The receptors were solubilized from the membrane fraction in 1% MNG-3 (lauryl maltose neopentyl glycol) and 0.02% CHS (cholesteryl hemisuccinate), with 4 mM theophylline. The insoluble material was removed by centrifugation at 1,980×g for 5 min and the supernatant was incubated with TALON affinity chromatography resin (Takara-Clontech) overnight in the presence of 100 µM imidazole. The GPCRs were eluted in the elution buffer [50 mM HEPES pH 7.4, 10 mM NaCl, 0.05% MNG-3, 0.002% (w/v) CHS, 300 mM imidazole] and subsequently concentrated to ~2 mg/mL using an Amicon centrifugation concentrator.

Yeast Cell Membrane Preparation

At the end of fermentation, the cell pellets were collected after centrifugation at 4,000×g for 15 min at 4° C. and then washed once with 50 mM HEPES, pH 7.4, 100 mM NaCl buffer. The cell pellets were resuspended into Receptor Lysis Buffer (50 mM HEPES buffer, 10% glycerol, 100 mM NaCl, 2.5 mM EDTA) using the ratio of cell pellets to buffer equal to 1:4. The cell pellets suspensions were disrupted by Microfluidizer high shear fluid processor (20 M psi, 3 cycles) while keeping them cool. The disrupted cell pellets were centrifuged at 9,720×g for 30 min at 4° C. to discard unbroken cells and cellular debris. The supernatants were the prepared yeast cell membrane (YCM).

Radioligand Binding Assay

Adenosine $A_1$ Receptor.

5 µL membrane aliquots were incubated in a total volume of 50 µL assay buffer (50 mM HEPES at pH 7.4, 100 mM NaCl) with different concentrations of [$^3$H] DPCPX at 20° C. for 120 min. Nonspecific binding was determined in the presence of 10 µM DPCPX. Incubation was terminated by rapid filtration performed on Whatman GF/C filter in a Millipore XX2702550 12 Position Vacuum Filtration Sampling Manifold and washed with buffer (50 mM HEPES at pH 7.4, 100 mM NaCl). The filter-bound radioactivity was determined by LS 6500 Multi-Purpose Scintillation Counter. A minimum of three independent experiments was performed, and the values were pooled to generate the mean curves of FIGS. 1A and 1B. See also see Wenjie Zhao, Xudong Wang, and L. Ye, Expression and Purification of Yeast-derived GPCR, Gα and Gβγ Subunits for Structural and Dynamic Studies. Bioprotocol, 2021. 10.

Membrane Samples.

NMR samples for membranes typically consisted of 270-300 µL volumes of the cell membrane in 50 mM HEPES buffer, 10% glycerol, 100 mM NaCl, 2.5 mM EDTA, doped with 10% $D_2O$ and different concentration ligands prepared in DMSO as needed.

Protein Samples.

NMR samples for receptors typically consisted of 270-300 µL volumes of receptors in 50 mM HEPES buffer, 0.1% MNG-3, 0.02% CHS, 100 mM NaCl, doped with 10% $D_2O$ and different concentration ligands prepared in DMSO as needed.

Regular $^1$H NMR.

All $^1$H experiments were performed on a 600 MHz Varian Inova spectrometer. For $^1$H NMR, the $H_2O$ signal was suppressed using the saturation pulse incorporated into a t2pul sequence with pw of 23.0 µs at the power level set to 58 db and slight changed was optimized for individual experiments through arrays.

STD Experiments and WaterLOGSY Experiments.

STD and WaterLOGSY experiments were conducted at a $^1$H frequency of 600 MHz using Varian Inova spectrometer. 5 mm diameter NMR tubes with a sample volume of 270-300 µL were used in all experiments. Solutions were buffered using a HEPES buffer corrected to pH 7.4 and 10% glycerol. The sample preparation is exemplified as follows, the compound (solution in DMSO-d6), 30 µL $D_2O$ was added to 240 µL membrane in an Eppendorf tube. The resulting solution was spun to ensure full mixing and transferred to a 5 mm NMR tube before the run. Both STD and WaterLOGSY spectra were recorded for each sample. WaterLOGSY spectra in the absence of protein receptor were recorded.

Dynamic Light Scattering (DLS)

Samples were centrifuged at 2000×g for 5 minutes. The resulting supernatant was passed through 0.22 µm syringe filters and diluted in a range from 10- to 100-fold. DLS measurements were performed with a Zetasizer Nano S (Malvern Instruments, Worchestershire, UK) containing a 3-mW He-Ne laser (λ=633 nm). All measurements were taken at room temperature in a half-volume glass cuvette. Each correlation function was collected using signal acquisition times of 180 seconds. DLS autocorrelation functions were converted into particle-size distributions using the "general modes" algorithm provided with the Zetasizer Nano S. The particle diameters represent those for spherical particles diffusing at the same rate as the suspended membrane fragments.

Results and Discussion

To demonstrate WaterLOGSY application for in-membrane GPCR, a well-established GPCR system ($A_1R$) was used (see Wenjie Zhao, Xudong Wang, and L. Ye, Expression and Purification of Yeast-derived GPCR, Gα and Gβγ Subunits for Structural and Dynamic Studies. *Bioprotocol*, 2021. 10). $A_1R$'s structure in complex with ligand adenosine is available as a structural reference (Draper-Joyce, C. J., et al., Structure of the adenosine-bound human adenosine $A_1$ receptor-Gi complex. Nature, 2018. 558(7711): p. 559-563. The receptor functionality in the MNG-3 reconstituted and native membrane systems were evaluated and compared using a radioligand binding assay as shown in FIGS. 1A and 1B. It was seen that the functionality of $A_1R$ was highly dependent on the receptor environment as the binding affinity exhibited an order-of-magnitude discrepancy in these two different systems. Of note, the procedures with respect to the preparations of the receptors in the MNG-3 are flowcharted in FIG. 2, in which the membrane used in this study refers to supernatant cell membrane after a low-speed centrifugation (8,000×g) and before the step of the ultracentrifugation (100,000×g).

Figure 3B:
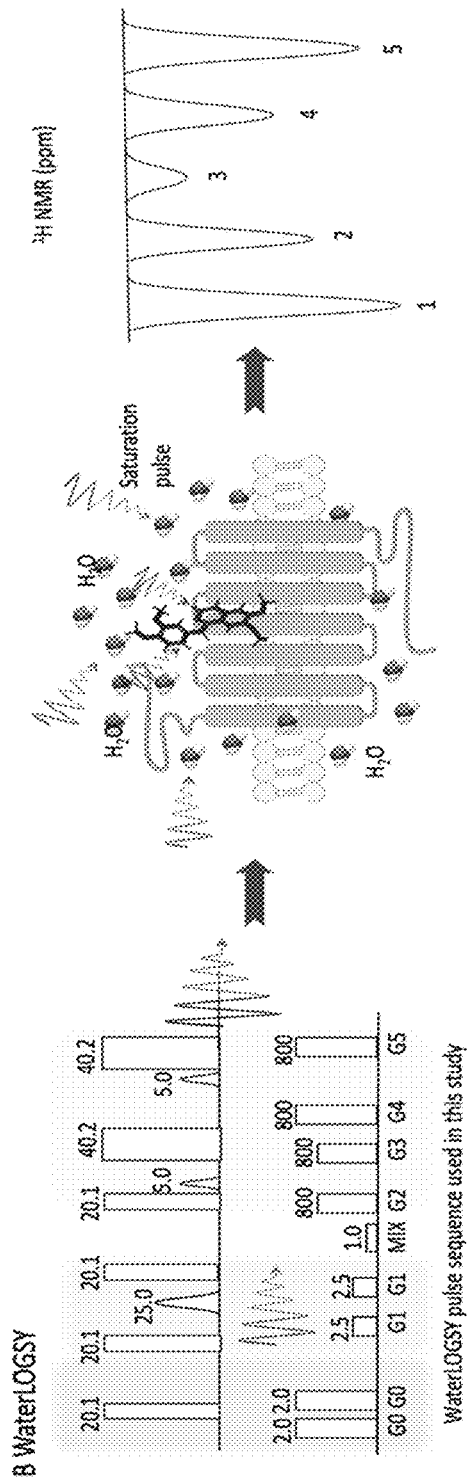
FIG. 3B is a schematic flowchart of WaterLOGSY NMR used for probing ligand orientation binding to receptor pocket. The "outwards" and "inwards" notation stand for the orientation of ligand towards the pocket. Of note, due to the intensity difference of these two spectra, the signals of WaterLOGSY spectrum are usually normalized to match regular $^1$H spectrum.

As shown in FIG. 3, a typical WaterLOGSY spectrum (FIG. 3B), along with a regular $^1$H NMR experiment (FIG. 3A) serving as a reference, were acquired in order to determine the ligand binding orientation. It was observed that buried protons of the ligand exhibited a decreased signal intensity in proportion to that in a regular $^1$H NMR, which serves as a control, after spectral normalization that depended on its depth towards the binding pocket (FIG. 3B). With this in mind, we examined adenosine binding to $A_1R$ receptors to acquire a STD spectrum in the MNG-3 reconstituted system, which serves as a reference. We expected that both STD and WaterLOGSY experiments would show the same ligand binding pattern.

Figure 5:
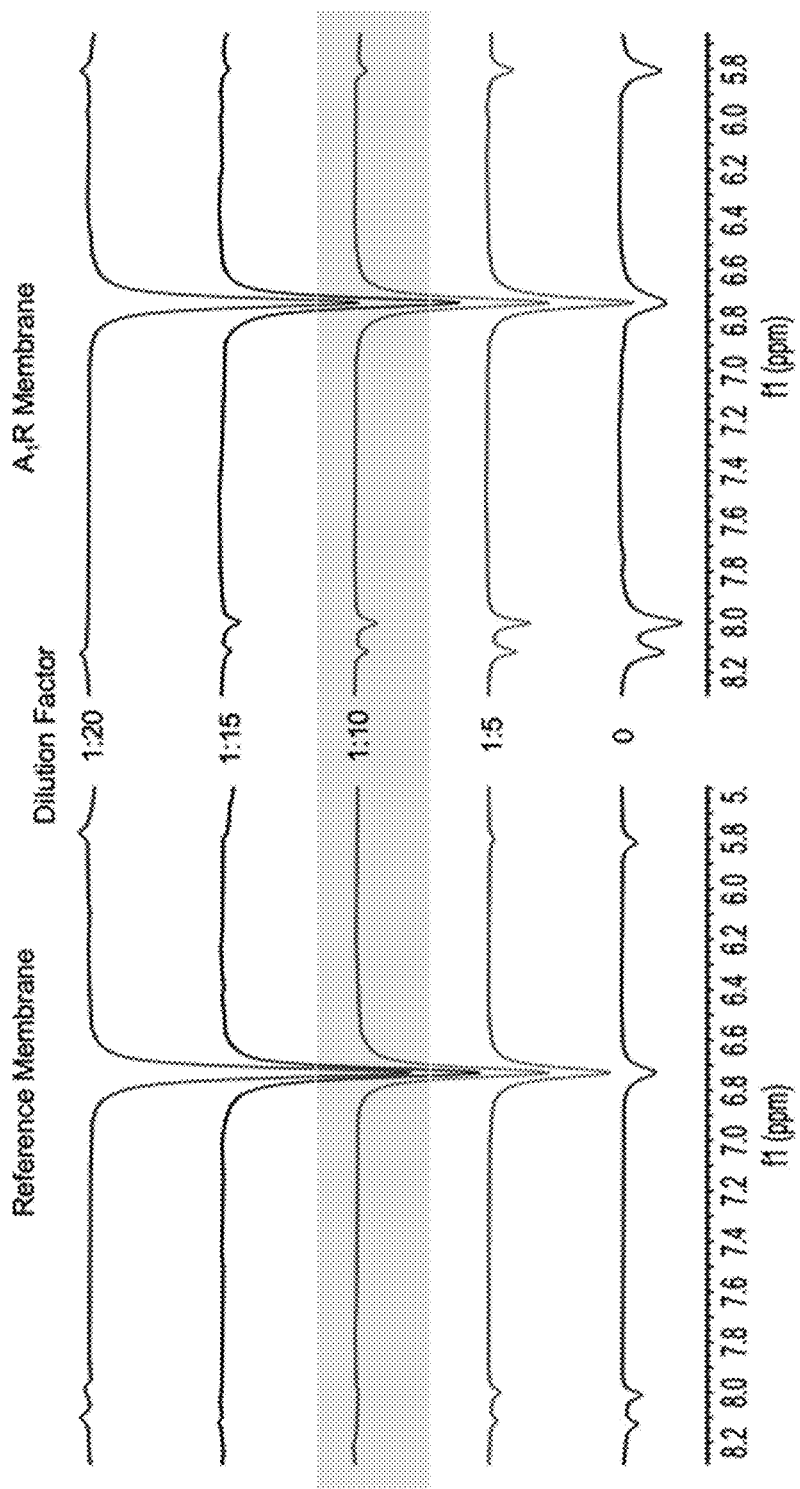
FIG. 5 has WaterLOGSY spectra that show WaterLOGSY NOE effects as a function of membrane dilution factors with and without target receptors (e.g., $A_1R$).
Figure 6:
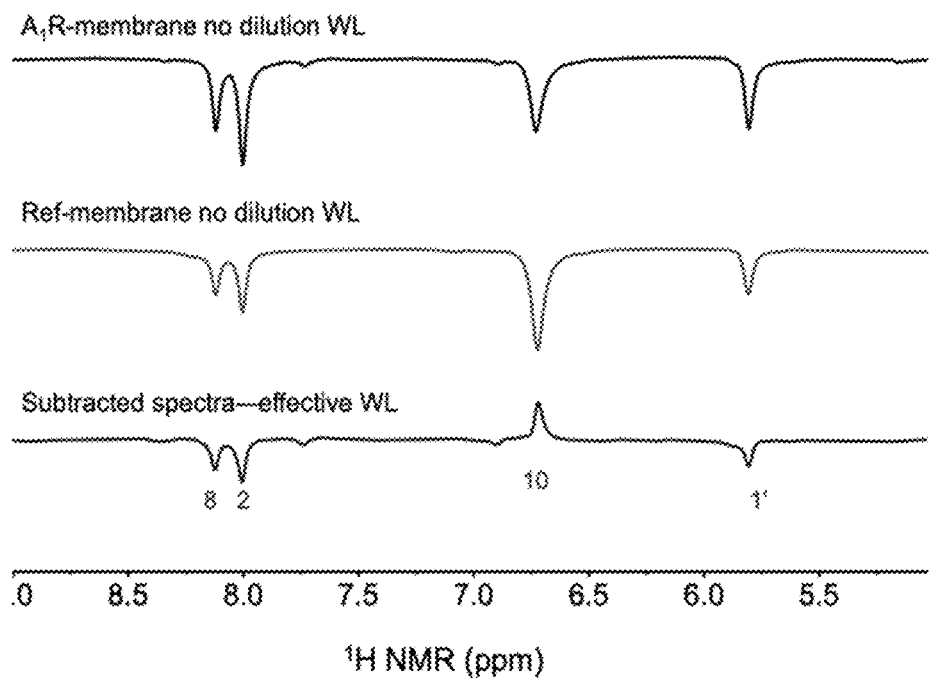
FIG. 6 has WaterLOGSY spectra. Subtracting reference membrane WaterLOGSY from $A_1R$ enriched membrane WaterLOGSY provides the effective WaterLOGSY spectrum.

As shown in FIG. 4A, proton 1' from the ribose group had the strongest STD signal, indicating it was deeply inserted into the binding pocket compared to protons 2, 8, and 10, in which protons 2 and 10 were relatively solvent exposed in comparison to proton 8. Consistently, as shown in FIG. 4B, analysis of WaterLOGSY spectrum confirmed an identical interaction pattern, in which NMR signal intensities appeared in a reversed order in comparison to the STD spectrum. Based on these findings, we moved on to apply WaterLOGSY in a native yeast cell membrane (YCM) from *Pichia pastoris*, a routinely GPCR expression system in our lab, using the MNG-3 reconstituted WaterLOGSY spectrum as the reference. To minimize the possible undesirable interaction between ligand and non-target proteins in membrane, membrane dilution experiments were performed. As shown in FIG. 5, it was clear that non-target NOE transfers could be minimized when the dilution factor reached 10 at which point the receptor-embedded membrane still exhibited strong WaterLOGSY negative NOE effects because the target receptors were enriched in the native membrane. Alternatively, the effective negative NOE could be obtained through WaterLOGSY spectral subtraction between the $A_1R$ membrane and reference membrane (FIG. 6) without dilution step. Both dilution and spectral subtraction strategies indicate the same binding pattern of adenosine to the $A_1R$ receptor. The WaterLOGSY spectra show that the orientation of the adenosine binding to the in-membrane receptor was identical to that in the detergent MNG-3 when non-specific binding was minimized or eradicated using either membrane dilution or spectral subtraction strategies. Specifically, the protons 1', 2, and 8 showed identical intensities in proportion compared to those obtained in the MNG-3, indicating the feasibility of using the in-membrane receptor as research target directly. Of note, proton 10 is from amino (—NH$_2$) group and it usually participates in hydrogen exchange with water, which can't be used as an indicator for WaterLOGSY evaluation.

Figure 7:
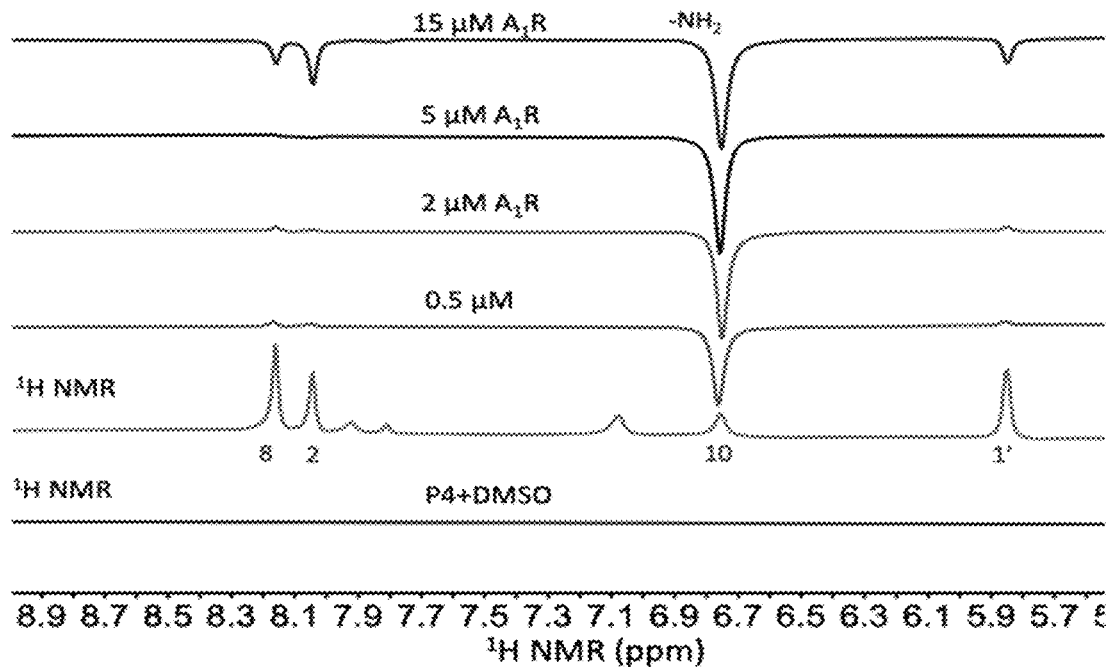
FIG. 7 has WaterLOGSY spectra as a function of $A_1R$ concentrations reconstituted in MNG-3.

It is feasible to use homogenized membrane studying the ligand-in-membrane receptor interaction. One of obvious advantages is 250 µL homogenized YCM (after microfluidization) was used in place of the 250 µL purified and reconstituted receptors. It is still extremely challenging to use the reconstituted GPCRs for drug screening as it is literally impossible to make 250 µL of the purified receptors for a vast majority of GPCRs at the µM level. We propose to use in-membrane GPCRs directly, which provides an avenue for screening drugs with minimal sample preparation. From a practical perspective, we were curious about what minimal concentration of membranes would be required for in-membrane WaterLOGSY data acquisition. As aforementioned in FIG. 5, 10× diluted membrane still allowed us to detect strong WaterLOGSY signals arising from the ligand-$A_1R$ interactions while minimizing the non-specific binding. Radioligand binding assay indicated the receptor concentration was around 10 nM at 10× times dilution. This makes it possible to perform 1,000 WaterLOGSY experiments with only 250 mL cell culture. In comparison, a series of WaterLOGSY spectra were also acquired as a function of concentration of the purified $A_1R$ receptors (FIG. 7). In the latter case, at least 15 µM of the purified $A_1R$ was required to observe a decent WaterLOGSY signal, making it challenging for a vast majority of GPCRs to even make one NMR sample from a 6 L cell culture. This dramatic difference can be attributed to the affinity discrepancy of the ligand to reconstituted and in-membrane receptors as shown in FIG. 1, resulting in magnetization cross-relaxation differ for ligand-receptor interactions in two settings.

Figure 8:
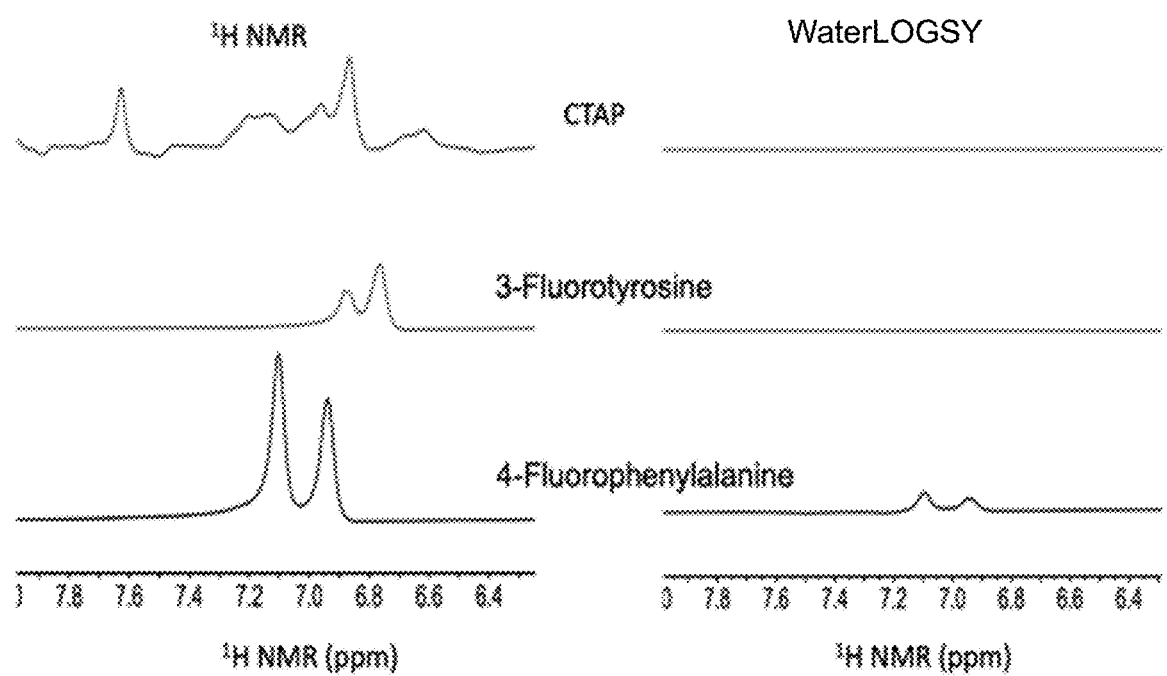
FIG. 8 has WaterLOGSY spectra for non-binders of the $A_1R$ receptor. These compounds exhibited either positive signals or no signals were detected for the compounds.
Figure 9:
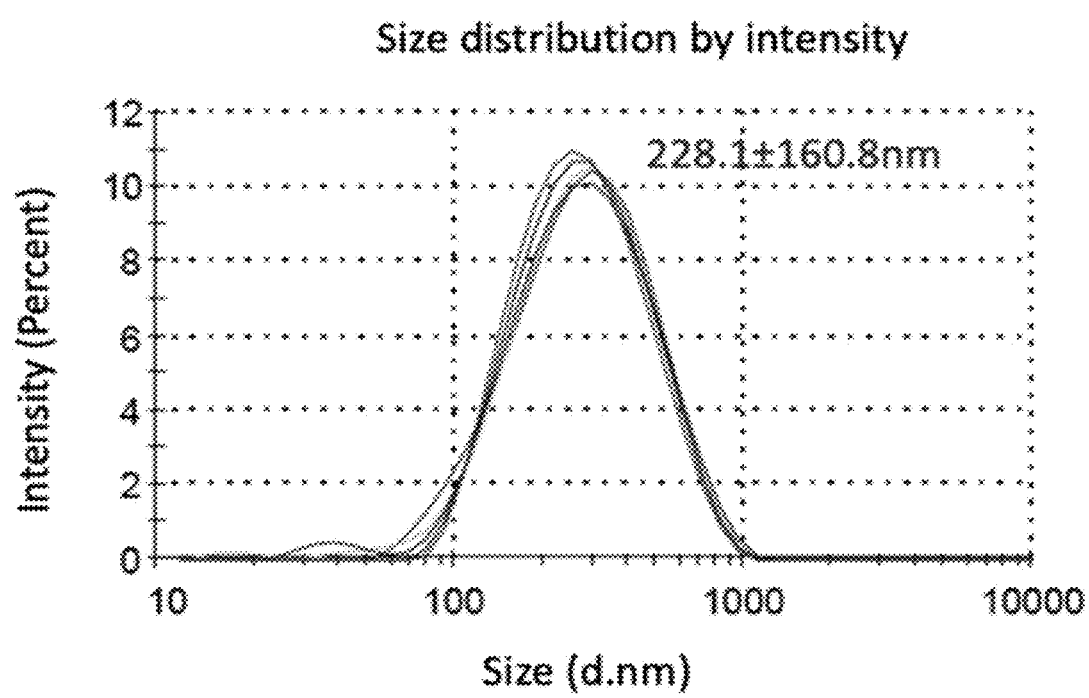
FIG. 9 is a plot showing dynamic light scattering measurements for receptor embedded yeast cell membranes.

Further, we tested several non-binders of the $A_1R$ receptor using 10× diluted $A_1R$ in YCM. As shown in FIG. 8, the non-binders could be well determined through either their positive NOEs (4-Fluorophenylalanine), resulting from non-specific binding interaction due to random interactions between ligand and the receptor, or in absence of obvious NOE signals (CTAP and 3-fluorotyrosine while specific ligand-receptor interaction will be presented as negative NOEs on the spectrum. Finally, dynamic light scattering measurements were performed to characterize the size of the membrane fragments in which the in-membrane receptors were embedded. As shown in FIG. 9, the experiments revealed that the size of the fractionalized membranes was in the range of 228.1±160 nm.

Figure 10:
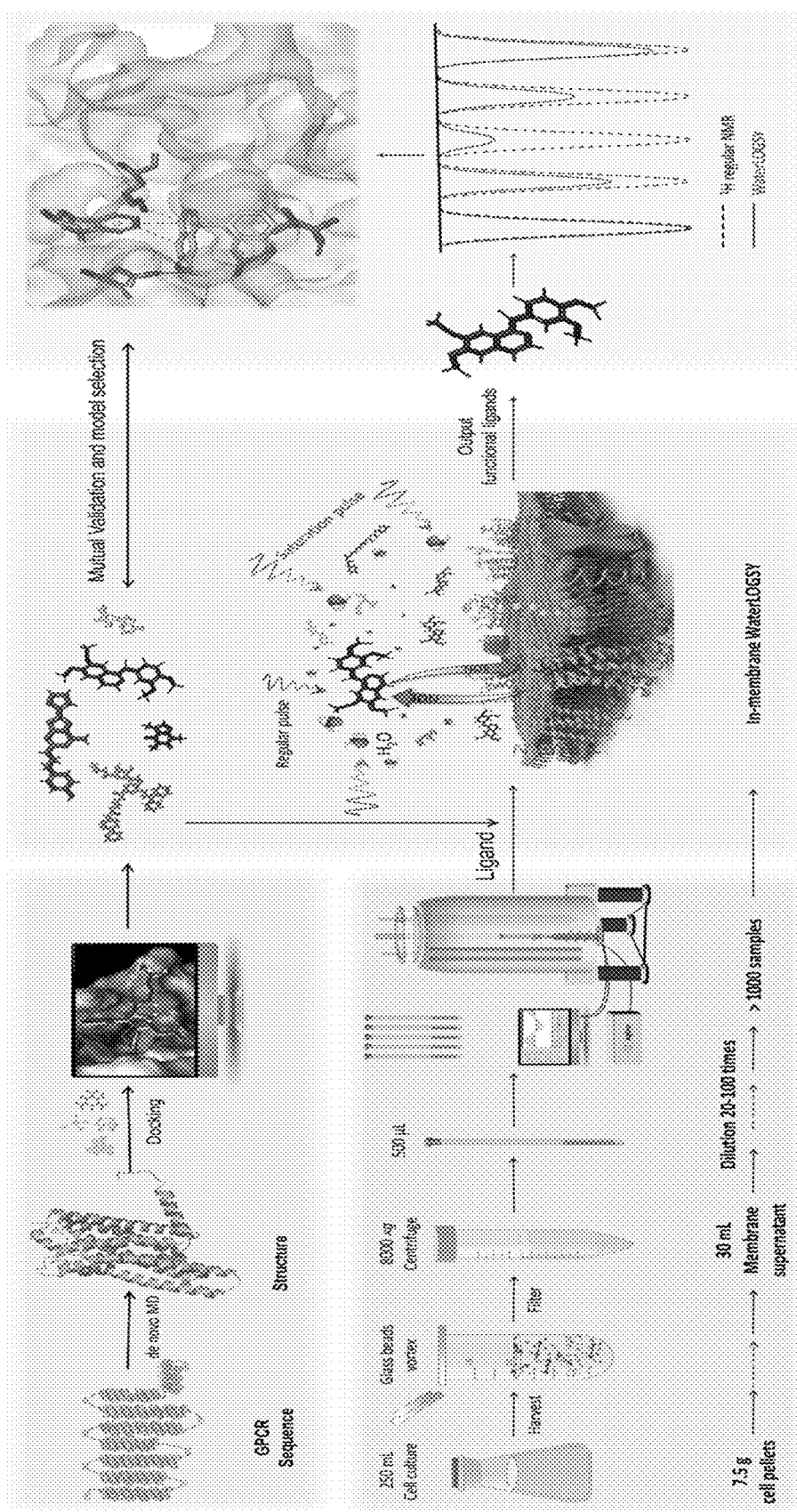
FIG. 10 is a schematic flowchart of a high-throughput in-membrane NMR platform integrated with de novo computational simulations. Using the $A_1R$ receptor as an example, 15 µM of the reconstituted receptors (prepared from 6 L cell culture) are required for one WaterLOGSY experiment whereas 250 mL cell culture allows us to perform more than 1,000 in-membrane WaterLOGSY experiments.

Our research presented here demonstrates the application of NMR spectroscopy to probe the ligand-receptor interaction using homogenized native membranes enriched with target receptors with potential applications for drug screening by circumventing the large-quantity receptor purification. This research further advances the study of intermolecular interactions from a traditional reconstituted system to a native membrane system with a high-throughput potential (FIG. 10) from the sample preparation perspective. The in-membrane NMR approach can also be used for assisting computational screening to select the docking models. Considering recent breakthroughs in using machine learning such as AlphaFold and RoseTTAFold, it is reasonable to expect that we are at the brink of being able to perform large-scale, reliable drug screening against novel targets whose structures have not been experimentally resolved. The work presented in this study will be crucial in assisting the validation of such predictions.

Example 2

Expression and Purification of Yeast-Derived GPCR, Gα and Gβγ Subunits

This protocol was modified and finalized based on Ye et al., 2016 and Ye et al. 2018b (Ye, L., Van Eps, N., Zimmer, M., Ernst, O. P. and Prosser, R. S. (2016), titled Activation of the $A_{2A}$ adenosine G-protein-coupled receptor by conformational selection. Nature 533(7602): 265-268; and Ye, L., Orazietti, A. P., Pandey, A. and Prosser, R. S. (2018b), titled High-Efficiency Expression of Yeast-Derived G-Protein Coupled Receptors and (19)F Labeling for Dynamical Studies. Methods Mol Biol 1688: 407-421, the contents of which are hereby incorporated by reference in their entirety) as well as current work.

Figure 11:
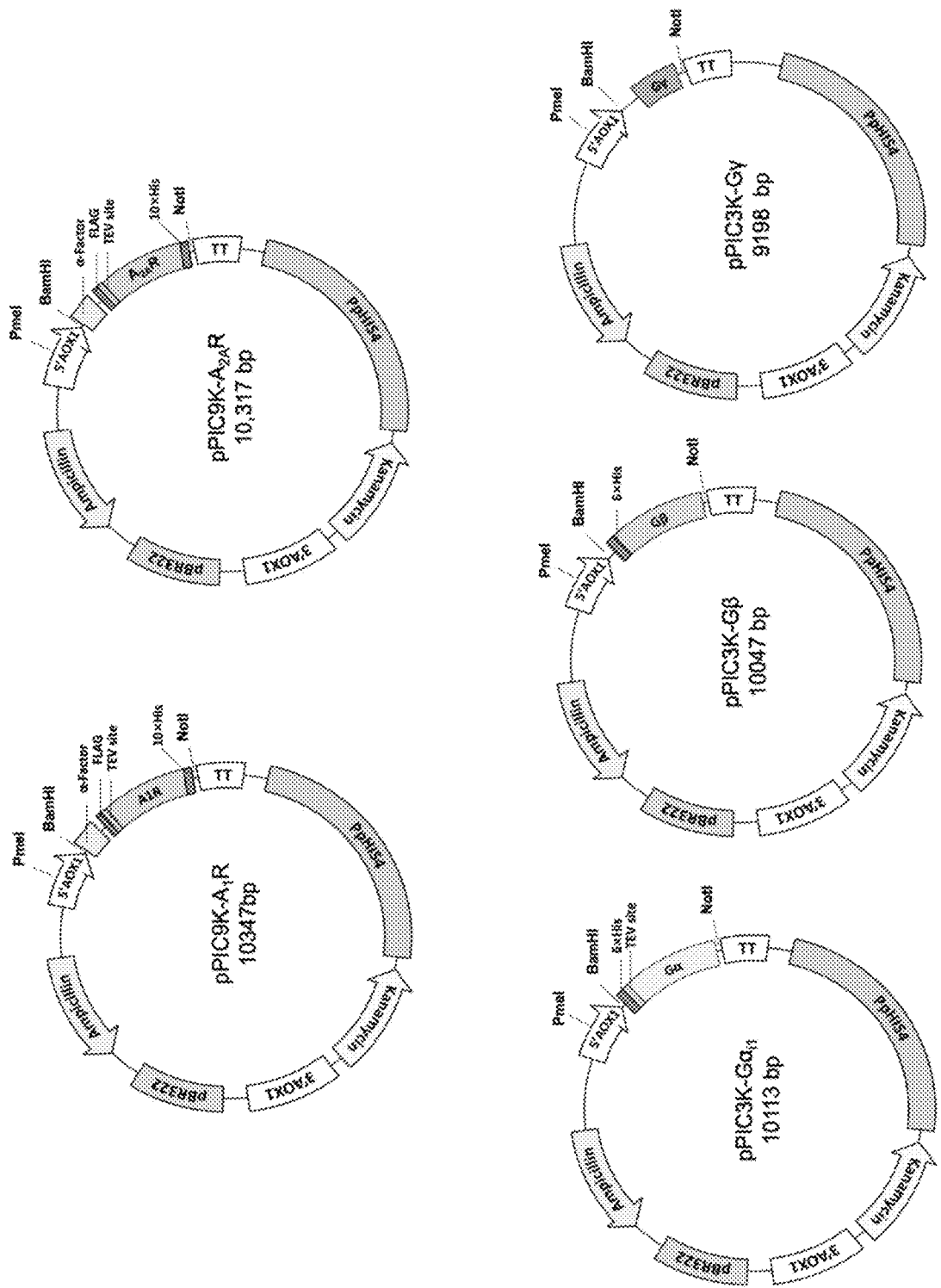
FIG. 11 has schematic diagrams of five plasmid constructs for GPCRs and G proteins.

All target genes presented in this protocol were codon optimized using online codon optimization software from the IDT web site (www.idtdna.com) and respective genes were synthesized prior to integration into the genome of *P. pastoris* via BamHI and NotHI restriction enzyme. In particular, both human derived adenosine $A_{2A}R$ (35.1 kDa) and $A_1$ receptor (36.5 kDa) genes had FLAG and His10 tags in the N- and C-terminal ends, respectively. In addition, following the FLAG tag, a TEV protease cleavage site as well as α-Factor peptide were inserted added to the front of genes (FIG. 11). In contrast, there was no FLAG tag and α-Factor sequences in Gα (45.7 kDa) as well as Gβ (38.7 kDa) and Gγ (7.6 kDa) constructs; in particular, there was no His-tag sequence in Gγ considering Gβ and Gγ were co-expressed together.

Materials and Methods

Plasmid Preparation for GPCRs and G Proteins

1 μL of the construct pPIC9K_ADORA2A, which was a recombinant vector of pPIC9K containing the ADORA2A receptor sequence, in a concentration of ~100 ng/μL, generously provided by T. Kobayashi (Japan) (examples of which can be found in Andre, N., Cherouati, N., Prual, C., Steffan, T., Zeder-Lutz, G., Magnin, T., Pattus, F., Michel, H., Wagner, R. and Reinhart, C. (2006), titled Enhancing functional production of G protein-coupled receptors in *Pichia pastoris* to levels required for structural studies via a single expression screen. Protein Sci 15(5): 1115-1126, the contents of which are hereby incorporated by reference in their entirety), was chemically transformed into 2 μL XL-10 Gold competent cells by heat shock for 45 s at 42° C.

200 μL of LB medium was immediately added into the mixture and the transformed cells was spread on the 25 mL LB plates containing 50 mg/mL ampicillin. The plates were incubated at 37° C. overnight.

One colony was picked from the plate and inoculated into 4 mL LB medium containing 50 mg/mL ampicillin and cultured overnight at 37° C. The plasmid was extracted using GenElute™ Plasmid Miniprep Kit following the instruction. The extracted plasmids were digested with 1 μL BamHI-HF and 1 μL NotI-HF with 1×NEB CutSmart® Buffer for 1.5 h in a 1.5 mL Eppendorf tube. 1 μL Quick CIP was added for additional 30 min digestion and phosphorylation to create pPIC9K backbone bearing BamHI and NotI restriction sites on each side. The total volumes were varied on the amounts of plasmids used. Usually, 1 μL of each restriction enzyme was used for the digestion of 20 μg plasmids.

All target gene fragments including $A_{2A}R$, $A_1R$, Gαs, Gβ, and Gγ (~200 ng/μL) were synthesized in accordance with *P. pastoris* codon optimized sequences. Of note, all gene fragments bearing BamHI and NotI restriction enzyme sites at N- and C-termini.

The gene fragments were also digested with 1 μL of each BamHI-HF and NotI-HF restriction enzymes with 1×NEB CutSmart® Buffer for 2 h without Quick CIP treatment.

Both digested pPIC9K plasmid and gene fragments were run DNA electrophoresis (as described in Krettler, C., Reinhart, C. and Bevans, C. G. (2013), titled Expression of GPCRs in *P. pastoris* for structural studies. Methods Enzymol 520: 1-29, the contents of which are hereby incorporated by reference in its entirety) and purified using QIAquick Gel Extraction Kit and the concentrations were measured using NanoDrop™ Lite spectrophotometer.

The ligation process was processed with various ratios between backbone plasmid and gene fragments using 1 μL T4 DNA Ligase with 1×NEB T4 DNA Ligase Buffer in a 0.2 mL PCR tube. The molar ratios between gene fragments and empty plasmids were set to 1:3, 1:1, and 3:1 with concentrations of gene fragments and empty plasmids of 10-100 ng/μL.

The ligated plasmids containing different gene fragments were transformed into XL-10 Gold competent cell (described in both Smbrook, J., Fritsch, E. F. and Maniatis, T. (1989), titled Molecular cloning: a laboratory manual, Cold Spring harbor laboratory.; and Dubnau, D. (1999), titled DNA uptake in bacteria. Annu Rev Microbiol 53: 217-244, the contents of which are hereby incorporated by reference in their entirety) and spread on the LB plates containing 50 mg/mL ampicillin. The plates were then incubated overnight at 37° C.

The plasmids for each construct were extracted using GenElute™ Plasmid Miniprep Kit. 20 μg plasmid in 100 μL for each construct was linearized with 1 μL PmeI restrict enzymes with 1×NEB CutSmart® Buffer for 2 h in a 0.2 mL PCR tube. 1,200 μL of 100% ethanol was added into the 100 μL linearized plasmids and incubated on the ice for 5 min.

The linearized plasmid was then centrifuged for 5 min at a speed of 16,200× g at 4° C. The supernatant was discarded, and the linearized DNA pellet was dried under Fume hood for 20 min before re-suspended in 20 μL of distilled water with DNA concentration around 1 μg/μL.

110 μL of linearized plasmids were mixed gently with 80 μL *P. pastoris* competent cells in 1.5 mL Eppendorf tube and kept on ice for 5 min prior to transfer into a 2 mm electroporation cuvette. The transformations were performed using a Gene Pulser II electroporation with the condition of 1,500 V charging voltage, 25 μF capacitance, and 400Ω resistance. 11 mL of ice-cold 1 M sorbitol was immediately added into the electroporation cuvette and transferred into 14 mL round-bottom tubes. The samples were then incubated for 3 h at 30° C. without shaking prior to spreading them onto YNBD plates. Of note, the linearized Gμ and Gγ plasmids (10 μL each) were transformed into the *P. pastoris* together while all other linearized plasmids were transformed separately.

Preparation of High-Yield Constructs for GPCRs and G Proteins

Figure 12A:
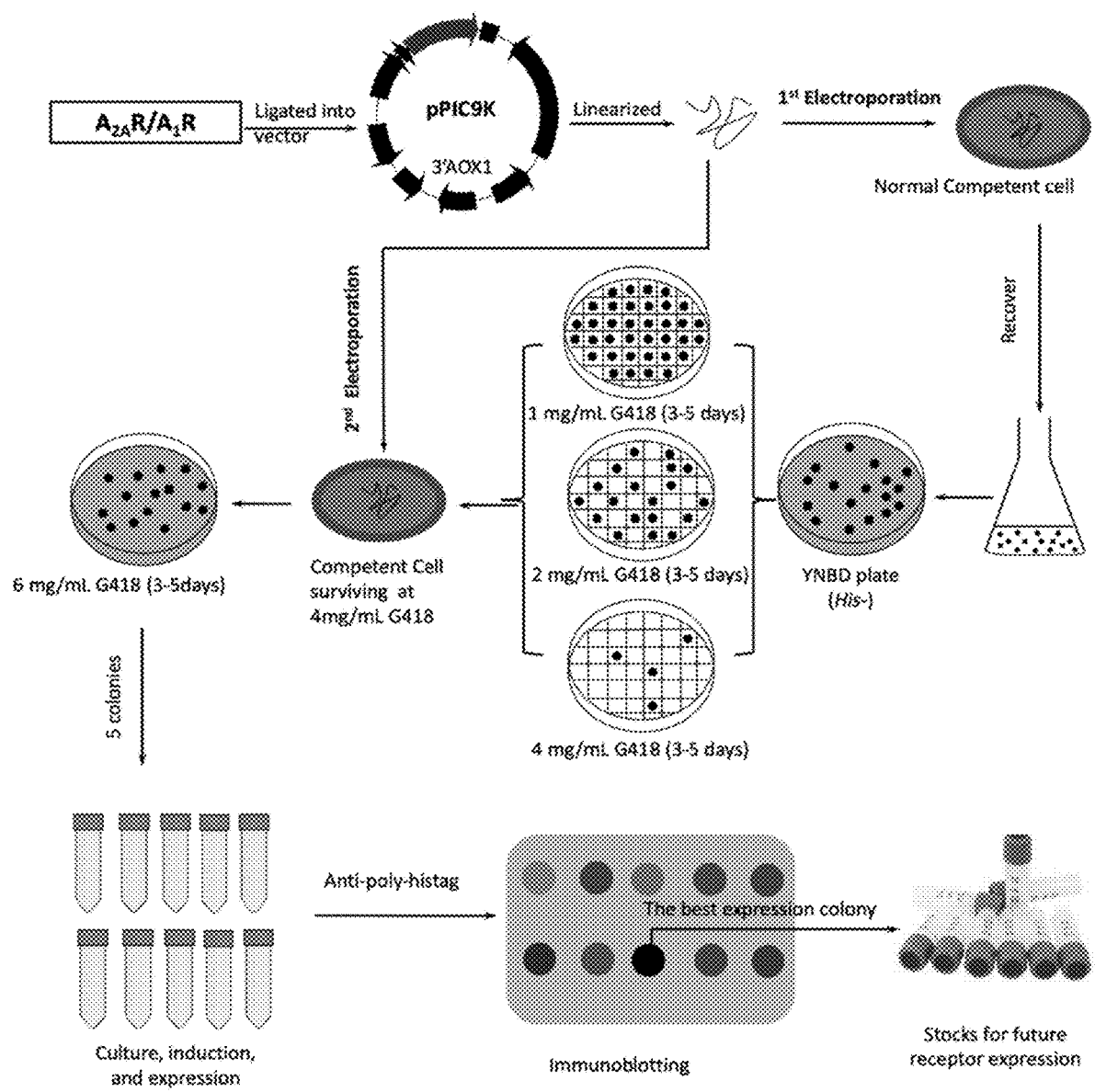
FIG. 12A is a schematic diagram depicting the electroporation procedure of construct screening for adenosine $A_{2A}R$ and $A_1R$ receptors.

As shown in FIG. 12A, the colonies grown on the YNBD plates after 3-5 days incubation would be transferred onto YPD plates containing 1 mg/ml G418 and incubated 3-5 days at 30° C. YPD plates with gradient G418 concentration were prepared and stored at 4° C. for subsequent screening.

The colonies grown on YPD plates containing 1 mg/mL G418 were further transferred onto second YPD plates containing 2 mg/mL G418. Incubated 3-5 days at 30° C. Consecutively, the colonies grown on YPD plates containing 2 mg/mL G418 were finally transferred onto YPD plates containing 4 mg/mL G418. Incubated additional 3-5 days at 30° C.

5-10 colonies on YPD plates containing 4 mg/mL G418 were picked for expression level evaluation using the immunoblotting assays against His10 and FLAG tags. Multiple integrated copies of pPIC9K can increase the Geneticin® resistance level from 0.5 mg/mL (1-2 copies) up to 4 mg/mL (7-12 copies).

The single colonies were inoculated into 4 mL BMGY medium in 14 mL Falcon tubes at 30° C. for at least 24 h with shaking (275 rpm) until $OD_{595}$=2.0-6.0. The medium was then transferred into 200 mL BMMY medium in 500 mL shake flasks covered by cotton plug.

The cells were continued culturing 60 h at 22° C. with shaking at 275 rpm. 0.5% methanol/12 h was added into the medium in order to induce and maintained the receptor or G protein expression. At the end of induction, the cell pellets were collected after centrifugation at 3,800×g for 10 min at 4° C. in 250 mL centrifuge bottles.

The cell pellets were washed once with Common Washing Buffer P1 in a ratio of 1:2. The cell pellets were then re-suspended into Receptor Lysis Buffer P2 using the ratio of cell pellets to buffer equal to 1:4. The cell pellets suspensions were then vortexed at 2,000 rpm for 2 h at 4° C. in the presence of a slurry of 5 mm glass beads. The disrupted cell pellets were centrifuged at 9,720×g for 30 min at 4° C. and the unbroken cells and cellular debris were discarded. The supernatant containing cell membrane was collected and applied to immunoblotting assays described in Gallagher, S. and Chakavarti, D. (2008), titled Immunoblot analysis (J Vis Exp(16). doi:10.3791/759), the contents of which are hereby incorporated by reference in its entirety.

For accuracy, immunoblotting was performed for both anti-His and anti-FLAG in response to the FLAG-tag and His-tags, respectively. 1 μL of supernatant was blotted on nitrocellulose membrane and allowed to dry. A second 1 μL of supernatant was applied to the previous position and let it dry. The membrane was placed in 20 mL Immunoblotting Blocking Buffer for 1 h at room temperature. The membrane was then transferred to 20 mL Immunoblotting Incubation Buffer containing either His-tag antibody (1:2,000) or FLAG-tag antibody (1:2,000) for 2 h.

The membrane was then washed three times with Immunoblotting Washing Buffer, followed by distilled water. The membrane was finally visualized by BM Blue POD substrate (3,3',5,5'-tetramethylbenzidine solution). The strongest intensity colonies were selected for further expressions. If the expression level was less than 0.5 mg/L cell culture, a second-cycle plasmid transformation was conducted following the instruction described in Procedure A and B. The colonies were directly screened on YPD plates containing 6 mg/mL G418 (F). The stocks of screened high-yield expression constructs were made with 20% autoclaved glycerol and frozen in the −80° C. freezer or Liquid Nitrogen.

Expression of GPCRs and G Proteins

Glycerol stocks of the transformants were inoculated onto YPD agar plates containing 0.1 mg/mL G418. 3-5 days later, a single colony was inoculated into 4 mL autoclaved YPD at 30° C. in 14 mL round bottom tubes with shaking at 275 rpm for 24 h. 4 mL medium was subsequently transferred into 200 mL autoclaved BMGY medium and cultured at 30° C. in 500 mL shake flask covered by aluminum foil with a shaking speed of 275 rpm till $OD_{595}$ reached 2-6, which would take about 24 h.

To induce expression, 200 mL cell pellets were spun down and transferred into 1 liter of autoclaved BMMY medium in 2.8 L flasks and cultured at 20° C. with a shaking speed of 275 rpm. Filtered methanol was added every 12 h with 0.5% (5 mL/L medium) if the baffled flasks were used. If the fermenter was used, the rate of methanol addition would be controlled at maximal 1 mL/h for each liter, which was dependent on the culture volume The cells for receptors expression were collected after 80 h fermentation while the cells for G proteins expression were collected after 60 h.

Purifications of GPCRs and G Proteins

The following sections describe the purification for GPCRs, Gα, and Gβγ proteins.

Purification of GPCRs

After 80 h expression, the cell pellets were collected at 3,800×g for 10 min at 4° C. in 250 mL centrifuge bottles. Cell pellets were washed once with Common Washing Buffer P1 in the ratio of 1 g cell pellets to 2 mL P1 and centrifuged at 3,800×g for 10 min at 4° C. in 250 mL centrifuge bottles. The washed cell pellets were re-suspended in Receptor Lysis buffer P2 in a ratio of 4:1 to ensure the suspension was sufficient in 250 mL centrifuge bottles.

The cells were then disrupted using the Microfluidizer for four cycles on the ice at the working pressure of 15,000 psi. The Microfluidizer was balanced with buffer P2 prior to the lysis. Intact cells and cell debris were separated from the membrane suspension at 9,720×g for 30 min at 4° C. in 250 mL centrifuge bottles. The supernatant was then collected and centrifuged at 100,000×g for 75 min using T45 rotor for the Beckman Ultracentrifuge with corresponding tubes.

The supernatant from ultracentrifugation was discarded and the membrane from different runs was collected together and suspended in Common Washing Buffer P1 to remove the EDTA. The supernatant from ultracentrifugation was discarded and the membrane pellets were dissolved in 50 mL conical centrifuge tube containing Receptor Preparation Buffer P3 and shaking at 4° C. until all membranes were dissolved sufficiently. The solution was centrifuged at 1,980×g for 5 min at 4° C. to remove the undissolved membrane.

The dissolved membranes were mixed with pre-balanced Talon Resin using Receptor Preparation Column Washing Buffer P4. Usually, 2 mL Talon Resin was used for 6 g membrane. Incubated for 2 h at 4° C. During the incubation, the imidazole was added to the final concentration of 100 μM. Two hours later, the Talon resin was packed onto a disposal column and washed with 5 column volumes of Receptor Preparation Column Washing Buffer P4.

Subsequently, the receptors were eluted from the column using the Column Elution Buffer P5 at a gravity rate. The eluted receptors were concentrated to 1 mL by Ultra-15 Centrifugal filters 3K and buffer change with 10 mL Receptor Preparation Column Washing Buffer P4 one time with a dilution factor of 10 at 4° C. with the speed of 3,846×g. The receptor then went through the XAC ligand column, which was pre-balanced using Receptor Preparation Column Washing Buffer P4. The XAC binding was repeated three times. The receptor bound XAC column was washed for 2 column volumes using Receptor Preparation Column Washing Buffer P4 to remove the non-functional receptors.

Figure 12B:
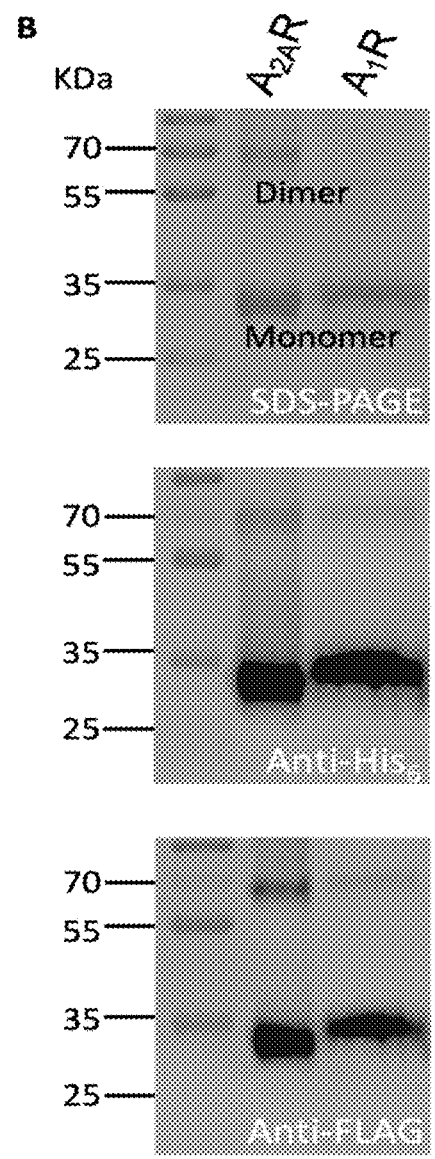
FIG. 12B is a series of images depicting SDS-PAGE and western blotting assays for screening of adenosine $A_{2A}R$ and $A_1R$ receptors.

The receptors were then eluted out using XAC Column Elution Buffer P6 consisting of Receptor Preparation Column Washing Buffer P4 with 25 mM theophylline. The eluted receptors were concentrated into 1 mL by Ultra-15 Centrifugal filters 3K and dialyzed against Receptor Preparation Column Washing Buffer P4 by Slide-A-Lyzer™ MINI Dialysis Devices 3.5K with a dilution factor of $1:10^6$ to remove all ligands to bring the receptor into the apo state. The purified receptors usually with 0.5-2 mg/L productivity were validated by SDS-PAGE (Laemmli, U. K. (1970), titled Cleavage of structural proteins during the assembly of the head of bacteriophage T4. Nature 227(5259): 680-685, the contents of which are hereby incorporated by reference in its entirety) as well as immunoblotting, as shown in FIG. 12B.

Purification of Gα

Cell pellets were harvested by centrifugation at 3,800×g for 10 min using the centrifuge at 4° C. in 250 mL centrifuge bottles. Cell pellets were washed once with Common Washing Buffer P1 in the ratio of 1 g cell pellets to 2 mL P1 and centrifuged with the speed of 3,800×g for 10 min at 4° C. in 250 mL centrifuge bottles. Cell pellets were re-suspended in G Protein Lysis buffer P2 in a ratio of 1:4. Cells were broken by Microfluidizer using 4 cycles at 15,000 psi for completely disrupting the yeast cell wall. The Microfluidizer was balanced with buffer P2 prior to the lysis.

The lysate was centrifuged at 4° C. for 30 min for 9,720×g in 250 mL centrifuge bottles. The supernatant was applied to Talon resins for 2 h, in which imidazole was added with a final concentration of 100 μM in order to decrease non-specific binding. The G protein bound Talon resins were applied to a disposal column. The packed column was then washed with 5 column volumes of G Protein Washing buffer P1.

Figures 13A, 13B, 13C:
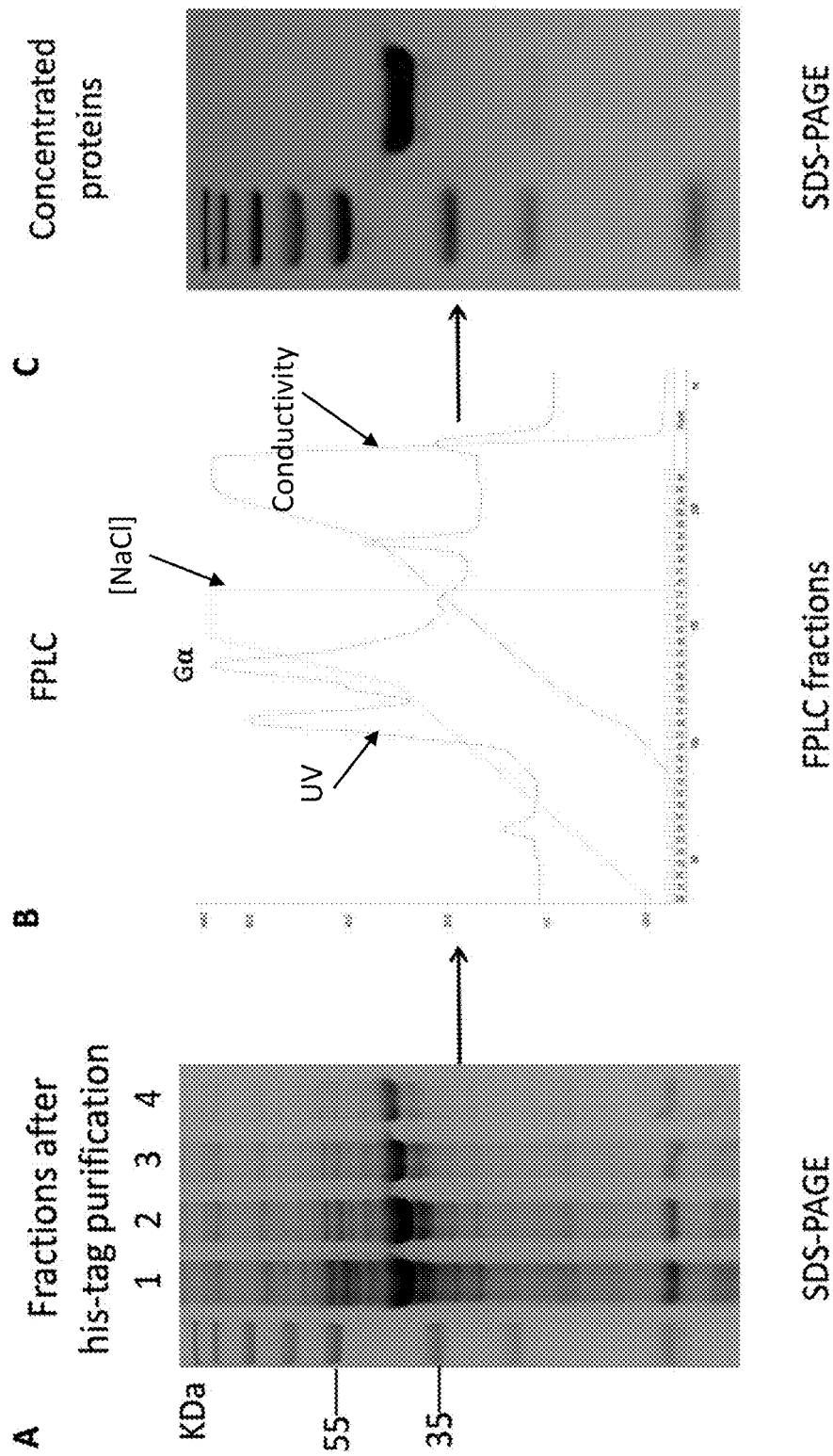
FIG. 13A is an image of an SDS-PAGE gel of his-tagged Gα protein purification fractions.
FIG. 13B is a chart of the FPLC elution program and resultant elution profiles for G protein purification.
FIG. 13C is an image of an SDS-PAGE gel of Gα protein FPLC purification fractions.

The target Gα was eluted with 10 mL G Protein Elution Buffer P3 at a gravity rate. Recycling the elution buffer to reduce the elution volume was optional. MgCl$_2$ was added to the final concentration of 1 mM as well as GDP of 50 μM. The Gα was concentrated to 2 mL by Ultra-15 Centrifugal filters, 3K at 4° C. with the speed of 3,846×g. The FPLC system was balanced with Buffer A-Gα for Q Sepharose Column prior to applying the eluted Gα protein into the system.
a. Q Buffer A-Gα: 50 mM HEPES, pH 8.0, 50 μM GDP, 1 mM MgCl$_2$
b. Q Buffer B-Gα: 50 mM HEPES, pH 8.0, 50 μM GDP, 1 mM MgCl$_2$, 1,000 mM NaCl FIGS. 13A and 13A show the results of the purification of yeast-derived Gα proteins. FIG. 13A shows an SDS-PAGE gel including purification fractions after His tag purification. FIG. 13B shows the elution program and resultant elution profile for Gα. FIG. 13C shows an SDS-PAGE gel including concentrated purification fractions from FPLC marked in FIG. 13B.

The Gα protein should be eluted with 20% of Q buffer B. The FPLC program for target Gα elution is shown in FIG. 13B and the Gα would be eluted out as shown in the graph, in which the flow rate, maximum column pressure, and fraction were set to 1.0 mL/min, 0.5 MPa, and 2.0 mL, respectively.

The corresponding fractions were collected and concentrated to 1 mL using Ultra-15 Centrifugal filters 3K at 4° C. with the speed of 3,846×g. The concentration of the Gα was measured using BCA kit with a productivity of 2-5 mg/L cell culture.

Purification of Gβγ

Cell pellets were harvested by centrifugation at 3,800×g for 10 min at 4° C. in 250 mL centrifuge bottles. The supernatant was discarded. Cell pellets were washed once with Common Washing Buffer P1 in the ratio of 1 g cell pellets to 2 mL P1 and centrifuged again at 3,800×g for 10 min at 4° C. in 250 mL centrifuge bottles. Cell pellets were washed one time with 1:2 ratio Common Washing Buffer P1 and centrifuged at 4° C. with the speed of 3,800×g for 10 min. The cell pellets were suspended in ice-cold G Protein Lysis Buffer P2.

The cell pellets were lysed by Microfluidizer for 4 cycles at pressure of 15,000 psi. The Microfluidizer was balanced with Buffer P2 prior to lysis. The lysed cell pellets were centrifuged at 9,720×g for 30 min to remove all debris and intact cells in 250 mL centrifuge bottles. The supernatant was applied to Talon resin for 2 h. Imidazole was added into the solution to a final concentration of 100 μM to decrease non-specific binding proteins.

Figure 14A:
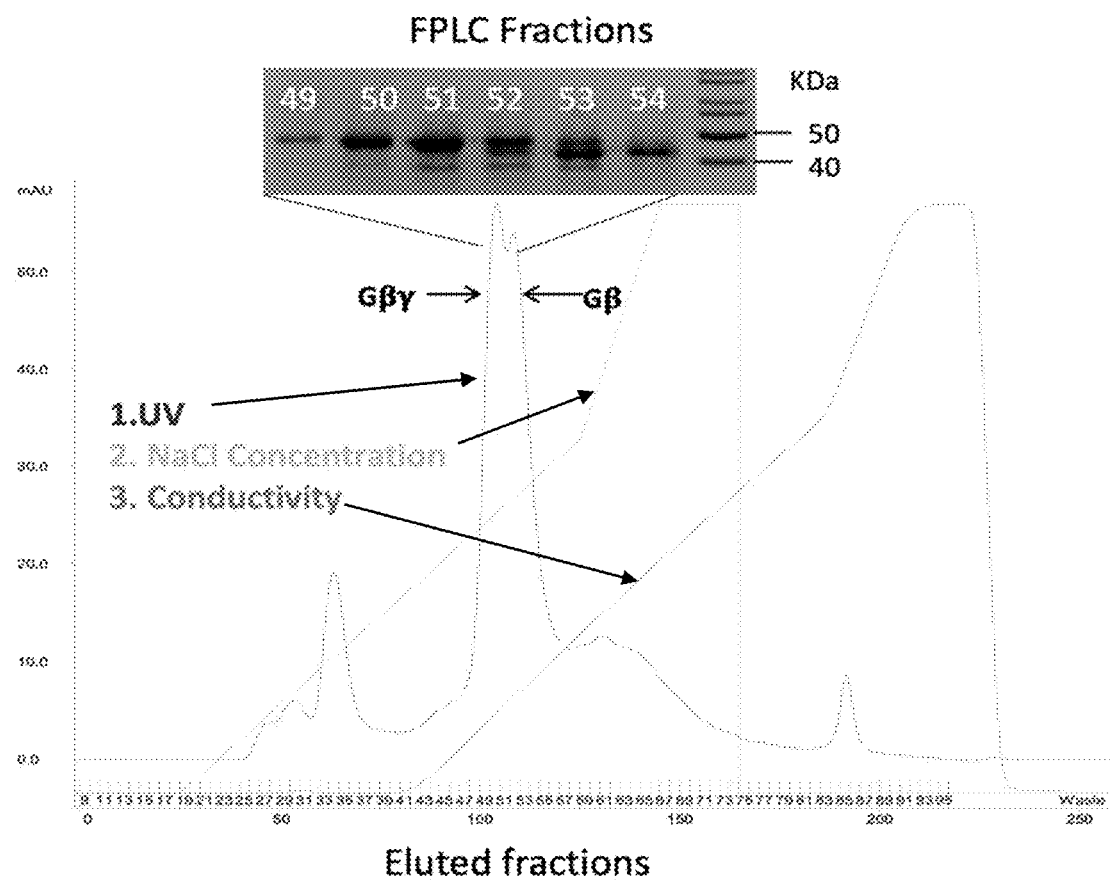
FIG. 14A is a chart of the FPLC elution program and resultant elution profiles for Gβγ and Gβ protein purification.
Figure 14B:
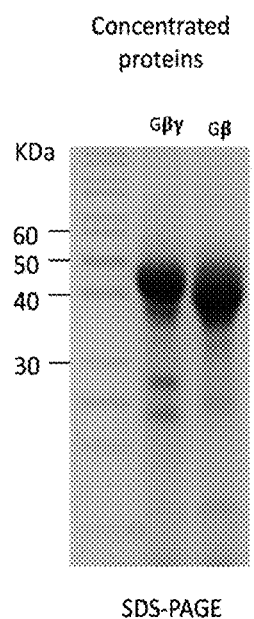
FIG. 14B is an image of an SDS-PAGE gel of Gβγ protein FPLC purification fractions.

FIGS. 14A and 14B depict elution programs and profiles of the purification of yeast-derived Gβγ proteins. The G protein bound resins were dispensed into a disposal column. The column was washed with 5 column volumes of Common Washing buffer P1. The Gβγ was gravity-eluted with 10 mL G Protein Elution Buffer. Recycling the elution buffer to reduce the elution volume was optional.

The Gβγ was concentrated to 2 mL by Ultra-15 Centrifugal filters 3K at 4° C. with the speed of 3,846×g. and changed the buffer into Q Sepharose High performance Buffer A-Gβγ. The sample was applied onto the FPLC and eluted with gradient elution with Q Sepharose High performance Buffer B-Gβγ (FIG. 14A). Fractions were collected using the same parameters for the Gα. The elution program and resultant elution profile for Gβγ are shown in FIG. 14A.

The eluted fractions were collected and concentrated with a productivity of 2-5 mg/L cell culture similar to Gα. The purity and molecular weight of proteins were validated using SDS-PAGE as shown in FIG. 14B, depicting the SDS-PAGE results for the concentrated fractions marked in FIG. 14A.

Recipes
1. 10× Phosphate buffer
   49.7 g Na$_2$HPO$_4$
   98.0 g NaH$_2$PO$_4$ in 1000 mL dH$_2$O, pH 6.5
2. Immunoblotting Blocking buffer
   125 mM NaCl
   25 mM Tris base, pH 7.5, 0.3% Tween-20 and 3% non-fat milk
3. Immunoblotting Incubation buffer
   Anti-His/Anti-Flag antibody diluted to 1:2,000 with blocking buffer
4. Immunoblotting Washing buffer
   125 mM NaCl
   25 mM Tris base, pH 7.5
   0.3% Tween-20
5. LB plates
   2.5% LB broth
   1.5% Agar
6. YNBD plates
   1.34% Yeast Nitrogen based w/o amino acid
   0.0004% D-Biotin
   1% Dextrose
   1.5% Agar
7. YPD medium
   1% Yeast extract
   2% Peptone
   2% Dextrose
8. YPD agar plates
   1% Yeast extract
   2% Peptone
   2% Glucose
   2% Agar
9. BMGY medium
   1% (w/v) Yeast extract
   2% (w/v) Peptone
   1.34% (w/v) YNB without amino acids
   0.00004% (w/v) Biotin
   1% (w/v) Glycerol
   0.1 M Phosphate buffer at pH 6.5
10. BMMY medium
    1% (w/v) Yeast extract
    2% (w/v) Peptone
    1.34% (w/v) Yeast nitrogen base without amino acids
    0.00004% (w/v) Biotin
    0.5% (w/v) Methanol
    0.1 M Phosphate buffer at pH 6.5
    0.04% (w/v) Histidine and 3% (v/v) DMSO 10 μM Theophylline
11. Common Washing Buffer P1
    20 mM Bis-tris, pH 6.5 (50 mM HEPES, pH 7.4)
12. Receptor Lysis Buffer P2
    20 mM Bis-tris, pH 6.5 (50 mM HEPES, pH 7.4)
    2.5 mM EDTA
    10% Glycerol
13. Receptor Preparation Buffer P3
    20 mM Bis-tris, pH 6.5 (50 mM HEPES, pH 7.4)
    100 mM NaCl
    1% MNG-3 and 0.02% CHS
14. Receptor Preparation Column Washing Buffer P4
    20 mM Bis-tris, pH 6.5 (50 mM HEPES, pH 7.4)
    100 mM NaCl
    0.1% MNG-3 and 0.002% CHS
15. Column Elution Buffer P5
    20 mM Bis-tris, pH 6.5 (50 mM HEPES, pH 7.4)
    100 mM NaCl
    0.1% MNG-3
    0.002% CHS
    300 mM Imidazole
16. XAC Column Elution Buffer P6
    20 mM theophylline in Receptor Preparation Column Washing Buffer P4
17. G Protein Washing Buffer P1
    50 mM HEPES, pH 8.0
18. G Protein Lysis buffer P2
    50 mM HEPES, pH 8.0
    10% Glycerol
    100 mM NaCl
19. G Protein Elution Buffer P3
    50 mM HEPES, pH 8.0, 300 mM imidazole
20. Q Buffer A-Gα
    50 mM HEPES, pH 8.0
    50 μM GDP
    1 mM MgCl$_2$
21. Q Buffer B-Gα
    50 mM HEPES, pH 8.0
    50 μM GDP
    1 mM MgCl$_2$
    1,000 mM NaCl
22. Q Buffer A-Gβγ
    20 mM Bis-tris, pH 6.5 (50 mM HEPES, pH 8.0)
23. Q Buffer B-Gβγ
    20 mM Bis-tris, pH 6.5 (50 mM HEPES, pH 8.0)
    1,000 mM NaCl
24. Immunoblotting Blocking Buffer
    125 mM NaCl
    25 mM Tris base, pH 7.5
    0.3% Tween-20
    3% Non-fat milk
25. Immunoblotting Washing Buffer
    125 mM NaCl
    25 mM Tris base, pH 7.5
    0.3% Tween-20
26. Radioligand Binding/Washing Buffers
    25 mM HEPES, pH 7.4
    100 mM NaCl

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of screening at least one ligand for binding to an in-membrane protein, the method comprising:
    contacting an in-membrane protein with the at least one ligand;
    detecting one or more NMR signals of the at least one ligand using WaterLOGSY; and
    detecting one or more NMR signals of the at least one ligand using regular 1H NMR,
    wherein a decrease in one or more NMR signals of the at least one ligand obtained using WaterLOGSY relative to the NMR signals of the at least one ligand obtained using regular $^1$H NMR indicates that the at least one ligand binds to the in-membrane protein.

2. The method of claim 1, wherein the method comprises use of high-throughput screening.

3. The method of claim 1, wherein the in-membrane protein is selected from: an adhesion protein, a selectin, a receptor, and an ion channel.

4. The method of claim 1, wherein the in-membrane protein is a G protein-coupled receptor (GPCR) prepared by disrupting cell membranes of a cell culture that expresses the GPCR and removing debris.

5. A method of identifying a ligand able to bind to an in-membrane protein, the method comprising:
    contacting an in-membrane protein with the ligand; and
    detecting one or more NMR signals of the ligand using WaterLOGSY; and
    detecting one or more NMR signals of the ligand using regular $^1$H NMR,
    wherein a decrease in one or more NMR signals of the ligand obtained using WaterLOGSY relative to the NMR signals of the ligand obtained using regular $^1$HNMR indicates that the ligand binds to the in-membrane protein.

6. A method of detecting binding of a ligand to an in-membrane protein, the method comprising:
    contacting an in-membrane protein with the ligand;
    detecting one or more NMR signals of the ligand using WaterLOGSY; and
    detecting one or more NMR signals of the ligand using regular 1H NMR,
    wherein a decrease in the one or more NMR signals of the ligand obtained using WaterLOGSY relative to the one or more NMR signals of the ligand obtained using regular $^1$HNMR indicates that the ligand binds to the in-membrane protein.

7. The method of claim 6, wherein the method comprises use of high-throughput screening.

8. The method of claim 7, wherein the ligand is from a library of ligands.

9. The method of claim 6, wherein the in-membrane protein is selected from: an adhesion protein, a selectin, a receptor, and an ion channel.

10. The method of claim 6, wherein the in-membrane protein is a G protein-coupled receptor (GPCR) prepared by disrupting cell membranes of a cell culture that expresses the GPCR and removing debris.

11. The method of claim 6, wherein the method further comprises subtracting one or more signals of the WaterLOGSY spectrum of the ligand in the presence of a membrane fragment from one or more NMR signals from a WaterLOGSY spectrum of the ligand in the presence of the in-membrane protein.

12. The method of claim 6, wherein the in-membrane protein is diluted about 5 to about 20 fold.

\* \* \* \* \*